(12) United States Patent
Lamborne et al.

(10) Patent No.: US 8,241,330 B2
(45) Date of Patent: Aug. 14, 2012

(54) SPINOUS PROCESS IMPLANTS AND ASSOCIATED METHODS

(75) Inventors: Andrew Lamborne, Golden, CO (US);
Michael Fulton, Superior, CO (US);
Jeffery Thramann, Longmont, CO (US)

(73) Assignee: Lanx, Inc., Broomfield, CO (US)

( * ) Notice: Subject to any disclaimer, the term of this patent is extended or adjusted under 35 U.S.C. 154(b) by 1217 days.

(21) Appl. No.: 11/934,604

(22) Filed: Nov. 2, 2007

(65) Prior Publication Data

US 2008/0183211 A1 Jul. 31, 2008

Related U.S. Application Data

(60) Provisional application No. 60/884,581, filed on Jan. 11, 2007, provisional application No. 60/912,273, filed on Apr. 17, 2007.

(51) Int. Cl.
*A61B 17/70* (2006.01)
(52) U.S. Cl. ........................................ 606/248; 606/249
(58) Field of Classification Search .................. 606/246, 606/248, 249, 279, 247; 623/17.11, 17.16
See application file for complete search history.

(56) References Cited

U.S. PATENT DOCUMENTS

| | | | |
|---|---|---|---|
| 64,815 A | 12/1868 | Garrin | |
| 242,443 A | 6/1881 | Foote | |
| 465,161 A | 12/1891 | Chase | |
| 765,879 A | 7/1904 | Campbell | |
| 832,201 A | 10/1906 | Kistler | |
| 1,137,585 A | 4/1915 | Craig | |
| 1,331,737 A | 2/1920 | Ylisto | |
| 1,400,648 A | 12/1921 | Whitney | |
| 1,725,670 A | 8/1929 | Novack | |
| 1,737,488 A | 11/1929 | Zohlen et al. | |
| 2,137,121 A | 11/1938 | Greenwald | |
| 2,677,369 A * | 5/1954 | Knowles | 606/249 |
| 2,689,568 A | 9/1954 | Wakefield | |

(Continued)

FOREIGN PATENT DOCUMENTS

EP 1266606 A2 12/2002

(Continued)

OTHER PUBLICATIONS www.thefreedictionary.com, definition for "around" accessed on Oct. 6, 2011.*

(Continued)

*Primary Examiner* — Jan Christopher Merene
(74) *Attorney, Agent, or Firm* — Holland & Hart LLP

(57) ABSTRACT

The present invention provides spinous process implant and associated methods. In one aspect of the invention the implant limits the maximum spacing between the spinous processes. In another aspect of the invention, a spacer has at least one transverse opening to facilitate tissue in-growth. In another aspect of the invention, an implant includes a spacer and separate extensions engageable with the spacer. The spacer is provided in a variety of lengths and superior to inferior surface spacings. In another aspect of the invention, an implant includes a spacer and a cerclage element offset from the midline of the spacer in use so that the spacer defines a fulcrum and the cerclage element is operative to impart a moment to the vertebrae about the spacer. In another aspect of the invention, instrumentation for inserting the implant is provided. In other aspects of the invention, methods for treating spine disease are provided.

35 Claims, 10 Drawing Sheets

U.S. PATENT DOCUMENTS

| | | |
|---|---|---|
| 2,774,350 A | 12/1956 | Cleveland |
| 2,789,860 A | 4/1957 | Knowles |
| 3,025,853 A | 3/1962 | Mason |
| 3,039,468 A | 6/1962 | Price |
| 3,242,922 A | 3/1966 | Thomas |
| 3,409,013 A | 11/1968 | Berry |
| 3,626,535 A | 12/1971 | Ostrowsky et al. |
| 3,648,691 A | 3/1972 | Lumb et al. |
| 3,788,316 A | 1/1974 | Kim et al. |
| 3,789,852 A | 2/1974 | Kim et al. |
| 4,092,788 A | 6/1978 | Gowing |
| 4,369,770 A | 1/1983 | Bacal et al. |
| 4,409,968 A | 10/1983 | Drummond |
| 4,448,191 A | 5/1984 | Rodnyansky et al. |
| 4,570,618 A | 2/1986 | Wu |
| 4,599,086 A | 7/1986 | Doty |
| 4,636,217 A | 1/1987 | Ogilvie et al. |
| 4,892,545 A | 1/1990 | Day et al. |
| 5,010,879 A | 4/1991 | Moriya et al. |
| 5,011,484 A | 4/1991 | Breard |
| 5,062,850 A | 11/1991 | MacMillan et al. |
| 5,472,426 A | 12/1995 | Bonati et al. |
| 5,496,318 A | 3/1996 | Howland et al. |
| 5,503,617 A | 4/1996 | Jako |
| 5,609,634 A | 3/1997 | Voydeville |
| 5,609,636 A * | 3/1997 | Kohrs et al. ............. 623/17.16 |
| 5,645,599 A | 7/1997 | Samani |
| 5,658,335 A | 8/1997 | Allen |
| 5,702,453 A * | 12/1997 | Rabbe et al. ............. 623/17.16 |
| 5,800,550 A | 9/1998 | Sertich |
| 5,813,978 A | 9/1998 | Jako |
| 5,836,948 A | 11/1998 | Zucherman et al. |
| 5,860,977 A | 1/1999 | Zucherman et al. |
| 5,876,404 A | 3/1999 | Zucherman et al. |
| 5,989,256 A | 11/1999 | Kuslich et al. |
| 6,045,552 A | 4/2000 | Zucherman et al. |
| 6,048,342 A * | 4/2000 | Zucherman et al. ......... 606/249 |
| 6,068,630 A | 5/2000 | Zucherman et al. |
| 6,074,390 A | 6/2000 | Zucherman et al. |
| 6,090,112 A | 7/2000 | Zucherman et al. |
| 6,099,527 A | 8/2000 | Hochschuler et al. |
| 6,149,652 A | 11/2000 | Zucherman et al. |
| 6,152,926 A | 11/2000 | Zucherman et al. |
| 6,156,038 A | 12/2000 | Zucherman et al. |
| 6,183,471 B1 | 2/2001 | Zucherman et al. |
| 6,190,387 B1 | 2/2001 | Zucherman et al. |
| 6,200,322 B1 | 3/2001 | Branch et al. |
| 6,235,030 B1 | 5/2001 | Zucherman et al. |
| 6,238,397 B1 | 5/2001 | Zucherman et al. |
| 6,280,444 B1 | 8/2001 | Zucherman et al. |
| 6,332,882 B1 | 12/2001 | Zucherman et al. |
| 6,332,883 B1 | 12/2001 | Zucherman et al. |
| 6,375,682 B1 * | 4/2002 | Fleischmann et al. ..... 623/17.12 |
| 6,379,355 B1 | 4/2002 | Zucherman et al. |
| 6,398,811 B1 | 6/2002 | McKay |
| 6,419,676 B1 | 7/2002 | Zucherman et al. |
| 6,419,677 B2 | 7/2002 | Zucherman et al. |
| 6,451,019 B1 | 9/2002 | Zucherman et al. |
| 6,451,020 B1 | 9/2002 | Zucherman et al. |
| 6,451,021 B1 | 9/2002 | Ralph et al. |
| 6,478,796 B2 | 11/2002 | Zucherman et al. |
| 6,500,178 B2 | 12/2002 | Zucherman et al. |
| 6,514,256 B2 | 2/2003 | Zucherman et al. |
| 6,520,907 B1 | 2/2003 | Foley et al. |
| 6,582,433 B2 | 6/2003 | Yun |
| 6,599,294 B2 | 7/2003 | Fuss et al. |
| 6,626,944 B1 | 9/2003 | Taylor |
| 6,652,527 B2 | 11/2003 | Zucherman et al. |
| 6,652,534 B2 | 11/2003 | Zucherman et al. |
| 6,679,833 B2 | 1/2004 | Smith et al. |
| 6,695,842 B2 * | 2/2004 | Zucherman et al. ......... 606/249 |
| 6,699,246 B2 | 3/2004 | Zucherman et al. |
| 6,699,247 B2 | 3/2004 | Zucherman et al. |
| 6,712,819 B2 | 3/2004 | Zucherman et al. |
| 6,733,534 B2 | 5/2004 | Sherman |
| 6,746,485 B1 | 6/2004 | Zucherman et al. |
| 6,761,720 B1 | 7/2004 | Senegas |
| 6,796,983 B1 | 9/2004 | Zucherman et al. |
| 6,800,084 B2 | 10/2004 | Davison et al. |
| 6,902,566 B2 | 6/2005 | Zucherman et al. |
| 6,926,728 B2 | 8/2005 | Zucherman et al. |
| 6,946,000 B2 | 9/2005 | Senegas et al. |
| 6,966,929 B2 | 11/2005 | Mitchell |
| 6,989,011 B2 | 1/2006 | Paul et al. |
| 7,029,473 B2 | 4/2006 | Zucherman et al. |
| 7,048,736 B2 | 5/2006 | Robinson et al. |
| 7,083,649 B2 | 8/2006 | Zucherman et al. |
| 7,087,083 B2 | 8/2006 | Pasquet et al. |
| 7,101,375 B2 | 9/2006 | Zucherman et al. |
| 7,189,234 B2 | 3/2007 | Zucherman et al. |
| 7,201,751 B2 | 4/2007 | Zucherman et al. |
| 7,442,208 B2 | 10/2008 | Mathieu et al. |
| 7,585,316 B2 | 9/2009 | Trieu |
| 7,658,752 B2 | 2/2010 | Labrom et al. |
| 7,753,938 B2 | 7/2010 | Aschmann et al. |
| 2001/0007073 A1 | 7/2001 | Zucherman et al. |
| 2001/0012938 A1 | 8/2001 | Zucherman et al. |
| 2001/0016743 A1 | 8/2001 | Zucherman et al. |
| 2001/0016776 A1 | 8/2001 | Zuckerman et al. |
| 2001/0021850 A1 | 9/2001 | Zucherman et al. |
| 2001/0031965 A1 | 10/2001 | Zucherman et al. |
| 2001/0039452 A1 | 11/2001 | Zucherman et al. |
| 2002/0029039 A1 | 3/2002 | Zucherman et al. |
| 2002/0095154 A1 | 7/2002 | Atkinson et al. |
| 2002/0116000 A1 * | 8/2002 | Zucherman et al. ............ 606/61 |
| 2002/0183746 A1 | 12/2002 | Zucherman et al. |
| 2003/0040746 A1 | 2/2003 | Mitchell et al. |
| 2003/0045935 A1 | 3/2003 | Angelucci et al. |
| 2003/0065330 A1 | 4/2003 | Zucherman et al. |
| 2003/0083688 A1 | 5/2003 | Simonson |
| 2003/0139812 A1 * | 7/2003 | Garcia et al. ............. 623/17.11 |
| 2003/0153915 A1 | 8/2003 | Nekozuka et al. |
| 2003/0216736 A1 | 11/2003 | Robinson et al. |
| 2004/0024458 A1 | 2/2004 | Senegas et al. |
| 2004/0059339 A1 | 3/2004 | Roehm, III et al. |
| 2004/0093001 A1 | 5/2004 | Hamada |
| 2004/0097931 A1 | 5/2004 | Mitchell |
| 2004/0106995 A1 | 6/2004 | Le Couedic et al. |
| 2004/0138749 A1 | 7/2004 | Zucherman et al. |
| 2004/0138750 A1 | 7/2004 | Mitchell |
| 2004/0143270 A1 | 7/2004 | Zucherman et al. |
| 2004/0147937 A1 | 7/2004 | Dunbar, Jr. et al. |
| 2004/0153071 A1 * | 8/2004 | Zucherman et al. ............ 606/61 |
| 2004/0162617 A1 | 8/2004 | Zucherman et al. |
| 2004/0167520 A1 | 8/2004 | Zucherman et al. |
| 2004/0172135 A1 | 9/2004 | Mitchell |
| 2004/0193159 A1 | 9/2004 | Zucherman et al. |
| 2004/0199121 A1 | 10/2004 | Wenchell et al. |
| 2004/0199168 A1 | 10/2004 | Bertagnoli et al. |
| 2004/0220568 A1 | 11/2004 | Zucherman et al. |
| 2004/0249379 A1 | 12/2004 | Winslow et al. |
| 2005/0010296 A1 | 1/2005 | Mitchell |
| 2005/0010298 A1 | 1/2005 | Zucherman et al. |
| 2005/0101955 A1 | 5/2005 | Zucherman et al. |
| 2005/0113926 A1 | 5/2005 | Zucherman et al. |
| 2005/0125065 A1 | 6/2005 | Zucherman et al. |
| 2005/0143738 A1 | 6/2005 | Zucherman et al. |
| 2005/0143820 A1 | 6/2005 | Zucherman et al. |
| 2005/0143826 A1 | 6/2005 | Zucherman et al. |
| 2005/0149192 A1 | 7/2005 | Zucherman et al. |
| 2005/0149193 A1 | 7/2005 | Zucherman et al. |
| 2005/0149196 A1 | 7/2005 | Zucherman et al. |
| 2005/0154462 A1 | 7/2005 | Zucherman et al. |
| 2005/0165398 A1 | 7/2005 | Reiley |
| 2005/0192574 A1 | 9/2005 | Blain |
| 2005/0192586 A1 | 9/2005 | Zucherman et al. |
| 2005/0196420 A1 | 9/2005 | Zucherman et al. |
| 2005/0203512 A1 | 9/2005 | Hawkins et al. |
| 2005/0209603 A1 | 9/2005 | Zucherman et al. |
| 2005/0216087 A1 | 9/2005 | Zucherman et al. |
| 2005/0228383 A1 | 10/2005 | Zucherman et al. |
| 2005/0228384 A1 | 10/2005 | Zucherman et al. |
| 2005/0240182 A1 | 10/2005 | Zucherman et al. |
| 2005/0245929 A1 | 11/2005 | Winslow et al. |
| 2005/0245937 A1 | 11/2005 | Winslow |
| 2005/0261768 A1 | 11/2005 | Trieu |
| 2005/0288672 A1 | 12/2005 | Ferree |

| | | |
|---|---|---|
| 2006/0004447 A1 | 1/2006 | Mastrorio et al. |
| 2006/0015099 A1 | 1/2006 | Cannon et al. |
| 2006/0015181 A1 | 1/2006 | Elberg |
| 2006/0036246 A1 | 2/2006 | Carl et al. |
| 2006/0036258 A1 | 2/2006 | Zucherman et al. |
| 2006/0036324 A1 | 2/2006 | Sachs et al. |
| 2006/0058790 A1 | 3/2006 | Carl et al. |
| 2006/0064165 A1 | 3/2006 | Zucherman et al. |
| 2006/0064166 A1 | 3/2006 | Zucherman et al. |
| 2006/0089718 A1 | 4/2006 | Zucherman et al. |
| 2006/0106397 A1 | 5/2006 | Lins |
| 2006/0124247 A1 | 6/2006 | Collins et al. |
| 2006/0142761 A1 | 6/2006 | Landry et al. |
| 2006/0161154 A1 | 7/2006 | McAfee |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0235387 A1 | 10/2006 | Peterman |
| 2006/0235521 A1 | 10/2006 | Zucherman et al. |
| 2006/0235533 A1 | 10/2006 | Blain |
| 2006/0241601 A1 | 10/2006 | Trautwein et al. |
| 2006/0241610 A1 | 10/2006 | Lim et al. |
| 2006/0241757 A1 | 10/2006 | Anderson |
| 2006/0247623 A1 | 11/2006 | Anderson et al. |
| 2006/0247634 A1 | 11/2006 | Warner et al. |
| 2006/0247640 A1 | 11/2006 | Blackwell et al. |
| 2006/0259037 A1 | 11/2006 | Hartmann et al. |
| 2006/0264938 A1 | 11/2006 | Zucherman et al. |
| 2006/0264939 A1 | 11/2006 | Zucherman et al. |
| 2006/0265066 A1 | 11/2006 | Zucherman et al. |
| 2006/0265067 A1 | 11/2006 | Zucherman et al. |
| 2006/0271194 A1 | 11/2006 | Zucherman et al. |
| 2006/0382066 | 11/2006 | Thramann |
| 2006/0282079 A1 | 12/2006 | Labrom et al. |
| 2006/0293662 A1 | 12/2006 | Boyer, II et al. |
| 2007/0005064 A1 | 1/2007 | Anderson et al. |
| 2007/0010813 A1 | 1/2007 | Zucherman et al. |
| 2007/0032790 A1 | 2/2007 | Aschmann et al. |
| 2007/0043361 A1 | 2/2007 | Malandain et al. |
| 2007/0043362 A1 | 2/2007 | Malandain et al. |
| 2007/0043363 A1 | 2/2007 | Malandain et al. |
| 2307/0043363 | 2/2007 | Malandain et al. |
| 2007/0049934 A1 | 3/2007 | Edidin et al. |
| 2007/0049935 A1 | 3/2007 | Edidin et al. |
| 2007/0049943 A1 | 3/2007 | Moskowitz et al. |
| 2007/0055237 A1 | 3/2007 | Edidin |
| 2007/0055246 A1 | 3/2007 | Zucherman et al. |
| 2007/0055276 A1 | 3/2007 | Edidin |
| 2007/0073292 A1 | 3/2007 | Kohm et al. |
| 2007/0093825 A1 | 4/2007 | Ferree et al. |
| 2007/0093830 A1 | 4/2007 | Zucherman et al. |
| 2007/0106385 A1 | 5/2007 | Zucherman et al. |
| 2007/0142915 A1 | 6/2007 | Altarac et al. |
| 2007/0213829 A1 | 9/2007 | LeCouedic et al. |
| 2007/0225706 A1 | 9/2007 | Clark et al. |
| 2007/0225807 A1 | 9/2007 | Phan et al. |
| 2007/0233076 A1 | 10/2007 | Trieu |
| 2007/0260245 A1 | 11/2007 | Malandain et al. |
| 2007/0265623 A1 | 11/2007 | Malandain et al. |
| 2007/0270840 A1* | 11/2007 | Chin et al. ..................... 606/61 |
| 2007/0276372 A1 | 11/2007 | Malandain et al. |
| 2008/0058937 A1 | 3/2008 | Malandain et al. |
| 2008/0147190 A1* | 6/2008 | Dewey et al. .............. 623/17.16 |
| 2008/0147192 A1 | 6/2008 | Edidin et al. |
| 2008/0312741 A1 | 12/2008 | Lee et al. |
| 2010/0036419 A1 | 2/2010 | Patel et al. |
| 2010/0191287 A1* | 7/2010 | Bucci ............................ 606/249 |
| 2010/0222817 A1 | 9/2010 | Perez-Cruet et al. |
| 2011/0066186 A1* | 3/2011 | Boyer et al. .................. 606/249 |
| 2011/0264221 A1* | 10/2011 | Woodward et al. ......... 623/17.16 |
| 2011/0319936 A1* | 12/2011 | Gordon et al. ............... 606/248 |
| 2012/0016418 A1* | 1/2012 | Chin et al. .................... 606/249 |

FOREIGN PATENT DOCUMENTS

| | | |
|---|---|---|
| JP | 2003220071 A | 8/2003 |
| WO | 94/00062 | 1/1994 |
| WO | 2005/009300 A1 | 2/2005 |

OTHER PUBLICATIONS

Acta Orthop Scand article dated Jun. 1984, by Bostman O. Myllynen P. Riska EB.

International Searching Authority "Notification of Transmittal of the International Search Report and the Written Opinion of the International Searching Authority, or the Declaration" Dec. 10, 2008.

Notification of Transmittal of International Preliminary Report on Patentability Apr. 5, 2010.

Lee, Jangbo, et al., "An Interspinous Process Distractor (X Stop) for Lumbar Spinal Stenosis in Elderly Patients", J. Spinal Disord Tech., vol. 17, No. 1, Feb. 2004, pp. 72-77.

International Bureau, Notification Concerning Transmittal of International Preliminary Report on Patentability (Chapter 1 of the Patent Cooperation Treaty), May 10, 2007.

International Searching Authority Notification of Transmittal of the International Search Report and the Written Opinion of the International Searching Authority, or the Declaration Nov. 10, 2008.

Kyphon "X-Stop a Patient's Guide Lumbar Spinal Stenosis & X-Stop Interspinous Decompression".

Jeremy C Wang, MD. Regis W. Haid Jr., M.D., Jay S. Miller, M.D. and James C. Robinson, M.D "Comparison of CD Horizon Spire spinous process plate stabilization and pedicle screw fixation after anterior lumbar interbody fusion" Feb. 4, 2006.

Jeremy C Wang, MD., David Spenciner. P.E., Sc.M., and James C. Robinson, M.D. "Spire spinous process stabilization plate: biochemical evaluation of a novel technology" Feb. 4, 2006.

Ole Bostman, Pertti Myllynen & Erik B. Riska "Posterior spinal fusion using internal fixation with the Daab plate" pp. 310-314 1984.

F.L. Knowles "The Knowles Vertebral Support Orientation" pp. 551-554, Oct. 1958.

Kyphon X-Stop IPD System "The first minimally invasive solution to lumbar spine stenosis".

* cited by examiner

SPINOUS PROCESS IMPLANTS AND ASSOCIATED METHODS

CROSS-REFERENCE TO RELATED APPLICATIONS

This application claims the benefit of U.S. Provisional Application No. 60/912,273, filed Apr. 17, 2007 and U.S. Provisional Application No. 60/884,581, filed Jan. 11, 2007.

FIELD OF THE INVENTION

The present invention relates to spinous process implants and associated methods.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist. With age, spinal discs begin to break down, or degenerate resulting in the loss of fluid in the discs and consequently resulting in them becoming less flexible. Likewise, the disks become thinner allowing the vertebrae to move closer together. Degeneration may also result in tears or cracks in the outer layer, or annulus, of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions are collectively referred to herein as spine disease.

Conventionally, surgeons treat spine disease by attempting to restore the normal spacing between adjacent vertebrae. This may be sufficient to relieve pressure from affected nerve tissue. However, it is often necessary to also surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Although techniques for placing intervertebral spacers, plates, and pedicle screw fixation systems have become less invasive in recent years, they still require the placement of hardware deep within the surgical site adjacent to the spine. Recovery from such surgery can require several days of hospitalization and long, slow rehabilitation to normal activity levels.

More recently, investigators have promoted the use of motion preservation implants and techniques in which adjacent vertebrae are permitted to move relative to one another. One such implant that has met with only limited success is the artificial disc implant. These typically include either a flexible material or a two-piece articulating joint inserted in the disc space. Another such implant is the spinous process spacer which is inserted between the posteriorly extending spinous processes of adjacent vertebrae to act as an extension stop and to maintain a minimum spacing between the spinous processes when the spine is in extension. The spinous process spacer allows the adjacent spinous processes to move apart as the spine is flexed.

SUMMARY

The present invention provides a spinous process implant and associated methods.

In one aspect of the invention, an implant for placement between spinous processes of adjacent vertebrae includes a spacer and an extension. The spacer has sidewall generally parallel to its longitudinal axis and having superior and inferior surfaces operable to abut the spinous processes and maintain the spinous processes in spaced apart relationship. The extension projects from the spacer transverse to the longitudinal axis to lie generally alongside the spinous processes of adjacent vertebrae and engage the spinous processes to limit the maximum spacing between the spinous processes.

In another aspect of the invention, the extension includes an adjustable fastener.

In another aspect of the invention, the extension includes a removable fastener.

In another aspect of the invention, an implant for placement between spinous processes of adjacent vertebrae includes a spacer having at least one transverse opening communicating from at least one of a superior and inferior outer surface inwardly to facilitate tissue in-growth.

In another aspect of the invention, the spacer includes a hollow interior and a plurality of transverse openings communicating from the superior and inferior outer surfaces to the hollow interior to facilitate tissue growth.

In another aspect of the invention, the spacer includes a porous structure and the transverse openings comprise a plurality of pores.

In another aspect of the invention, an implant for placement between spinous processes of adjacent vertebrae of a spine includes a spacer and separate extensions engageable with the spacer at its ends. The spacer is provided in a variety of lengths and superior to inferior surface spacings.

In another aspect of the invention, an implant for placement between spinous processes of adjacent vertebrae of a spine includes a spacer and a cerclage element. The cerclage element is offset posteriorly of the midline in use so that the spacer defines a fulcrum and the cerclage element is extendible around a portion of a vertebra and operative to impart a moment to the vertebra about the spacer.

In another aspect of the invention, instrumentation includes two instruments each having a working portion tapering from a larger cross-sectional dimension nearer a handle to a smaller cross-sectional dimension near the free end. The free end of one of the instruments defines a hollow tip sized to engage the free end of the first instrument and sized to engage the hollow tip of the implant.

In another aspect of the invention, a method includes inserting a spacer between spinous processes of adjacent vertebrae to provide both an extension stop and a flexion stop.

In another aspect of the invention, a method includes inserting a spacer between spinous processes of adjacent vertebrae and connecting a cerclage element to the adjacent vertebrae to impart a moment to the vertebrae about the spacer.

In another aspect of the invention, a method includes inserting a tapered instrument between adjacent spinous processes; engaging a tip of a spinous process spacer with the tip of the tapered instrument and passing the engaged pair back between the adjacent spinous process to insert the spacer between the spinous processes.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Figure 1:
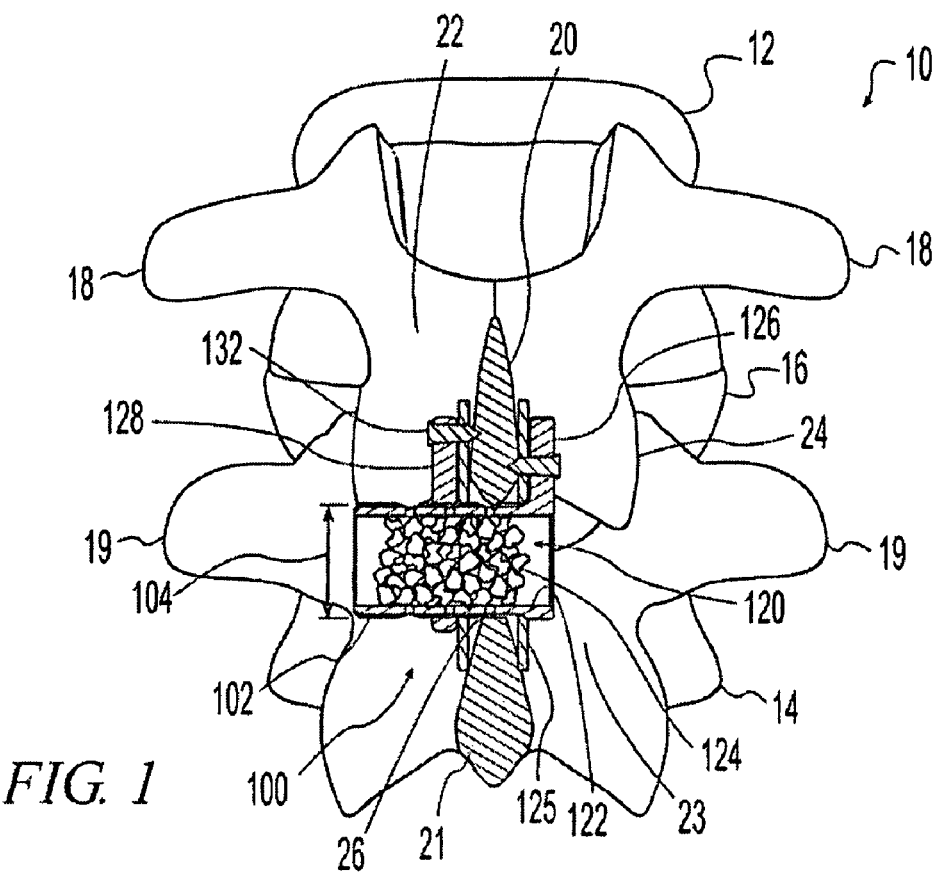
FIG. 1 is a cross sectional view of an implant according to the present invention in situ.

Embodiments of spinous process implants according to the present invention include a spacer and an extension extending outwardly from the spacer. The spinous process implant may be configured for insertion between adjacent spinous processes of the cervical, thoracic, and/or lumbar spine. The spacer may be provided in a variety of sizes to accommodate anatomical variation amongst patients and varying degrees of space correction. The spacer may include openings to facilitate tissue in-growth to anchor the spacer to the vertebral bodies such as tissue in-growth from the spinous processes. The spacer may be configured for tissue in-growth from superior and inferior spinous processes to cause fusion of the adjacent spinous processes. The openings may be relatively large and/or communicate to a hollow interior of the spacer. A hollow interior may be configured to receive bone growth promoting substances such as by packing the substances into the hollow interior. The openings may be relatively small and/or comprise pores or interconnecting pores over at least a portion of the spacer surface. The openings may be filled with bone growth promoting substances.

The spacer may have any suitable cross-sectional shape. For example, it may be cylindrical, D-shaped, C-shaped, H-shaped, include separated cantilevered beams, and/or any other suitable shape. The shape may include chamfers, fillets, flats, relief cuts, and/or other features to accommodate anatomical features such as for example the laminae and/or facets.

The extension may extend transversely from the spacer relative to a spacer longitudinal axis to maintain the spacer between adjacent spinous processes. A single extension may extend in one or more directions or multiple extensions may be provided that extend in multiple directions. One or more extensions may be adjustable longitudinally relative to one another and/or the spacer to allow the extensions to be positioned relative to the spinous processes. A moveable extension may be provided that is movable axially relative to the spacer and another extension. Alternatively, a plurality of moveable extensions may be provided. For example, the extensions may clamp against the sides of the spinous processes to immobilize the spinous processes relative to one another and promote fusion between the adjacent vertebrae. The extensions may include fasteners engageable with the spinous processes. The fasteners may include sutures, wires, pins, straps, clamps, spikes, screws, teeth, adhesives, and/or other suitable fasteners. The fasteners may be integrated into the extensions or they may be modular. Modular fasteners may be adjustable, replaceable, and/or removable to allow tailoring of the kind and quality of fixation from rigid fixation to no fixation. The spacer, extensions, and/or fasteners may advantageously be made of different materials. For example, the spacer and extensions may be made of a relatively softer material while the fasteners may be made of a relative harder material. For example, the spacer and/or extension may be made of a polymer and/or other relatively soft material and the fastener may be made of a metal and/or other relatively hard material.

Cerclage may be used to stabilize the spinous process implant and/or to provide other benefits. For example, wires, straps, bands, cables, cords, and/or other elongated members may encircle the pedicles, laminae, spinous processes, transverse processes, and/or other spinal structures. The cerclage may be relatively inextensible to provide a hard check to spine flexion or the cerclage may be relatively extensible to provide increasing resistance to flexion. The cerclage may be relatively flexible and drapeable such as a woven fabric or it may be relatively rigid such as a metal band. The cerclage may have shape memory properties that cause it to resume a prior set shape after implantation. The cerclage may be independent of the spinous process implant or may engage it. For example, the cerclage may pass through a hollow interior of the spinous process implant and/or engage the extension. The cerclage may be offset from the spacer and provide a tensioning force that uses the spacer as a fulcrum to offload the disc and/or open the disc space.

The implant may be supplemented with bone growth promoting substances to facilitate fusion of adjacent vertebrae between spinous processes, laminae, transverse processes, facets, and/or other spinal structures. The bone growth promoting substances may be spaced from the implant, placed adjacent the implant, sandwiched between the implant and underlying bone, placed inside the implant, coated onto the implant, and/or otherwise placed relative to the implant. If it is coated onto the implant it may cover the entire implant or only selected portions of the implant such as the extensions, fasteners, spinous process contacting portions of the spacer, and/or other portions.

As used herein, bone growth promoting substances may include bone paste, bone chips, bone strips, structural bone grafts, platelet derived growth factors, bone marrow aspirate, stem cells, bone growth proteins, bone growth peptides, bone attachment proteins, bone attachment peptides, hydroxylapatite, calcium phosphate, and/or other suitable bone growth promoting substances.

The implant and any associated cerclage or other components may be made of any suitable biocompatible material including among others metals, resorbable ceramics, non-resorbable ceramics, resorbable polymers, and non-resorbable polymers. Some specific examples include stainless steel, titanium and its alloys including nickel-titanium alloys, tantalum, hydroxylapatite, calcium phosphate, bone, zirconia, alumina, carbon, bioglass, polyesters, polylactic acid, polyglycolic acid, polyolefins, polyamides, polyimides, polyacrylates, polyketones, fluropolymers, and/or other suitable biocompatible materials and combinations thereof.

The spinous process implant may be used to treat spine disease in a variety of surgical techniques including superspinous ligament sacrificing posterior approaches, superspinous ligament preserving posterior approaches, lateral approaches, and/or other suitable approaches. The spinous process implant may be used to treat spine disease by fusing adjacent vertebrae or by preserving motion between adjacent vertebrae; It may include only an extension stop such as a spacer, only a flexion stop such as flexible cerclage elements, or both a flexion and extension stop. The spinous process implant may be used to reduce loads on the facet joints, increase spinous process spacing, reduce loads on the disc, increase anterior disc spacing, and/or otherwise treat spine disease. Anterior effects may be accomplished by tensioning spine elements posterior to the spacer to apply a mechanical advantage to the spinal construct. Techniques for the spinal process implant may include leaving the tissues at the surgical site unmodified or modifying tissues such as trimming, rasping, roughening, and/or otherwise modifying tissues at the implant site.

Figure 2:
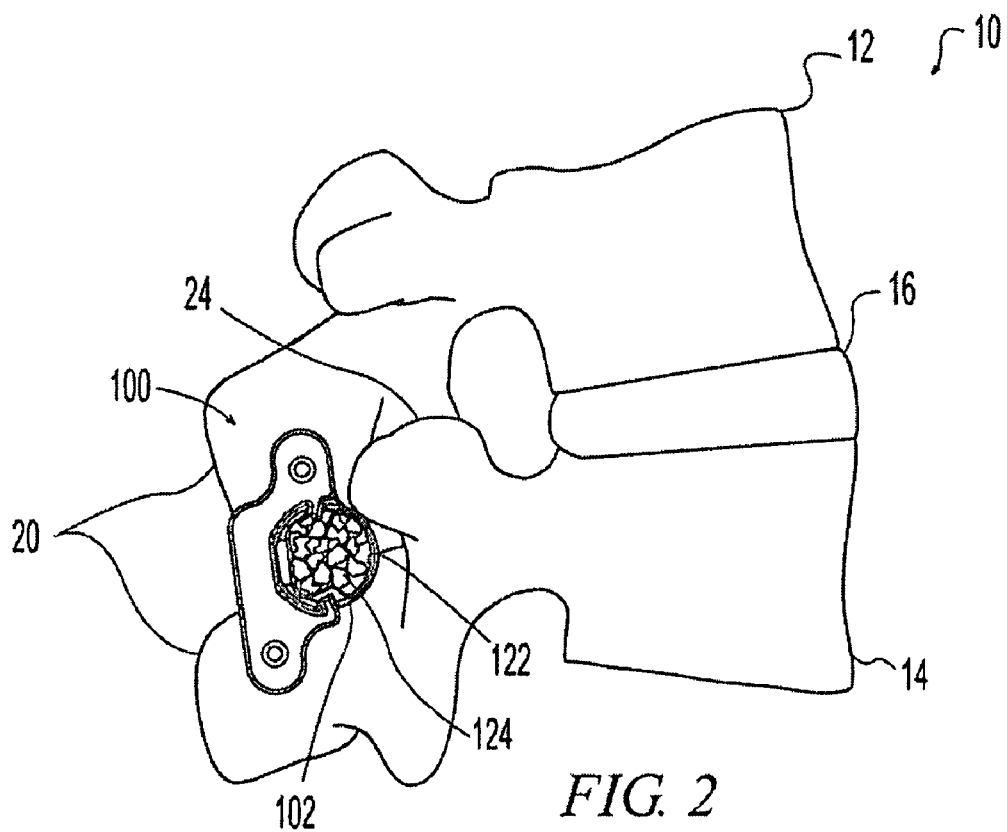
FIG. 2 is a side elevational view of the implant of FIG. 1 in situ.

FIGS. 1 and 2 depict posterior and lateral views of a pair of adjacent vertebrae of the lumbar spine 10. A superior vertebra 12 is separated from an inferior vertebra 14 by a disc 16. Each vertebra includes a pair of transverse processes 18, 19, a posteriorly projecting spinous process 20, 21, and a pair of laminae 22, 23 connecting the transverse processes 18, 19 to the spinous process 20, 21. In addition to the connection through the disc 16, the vertebrae 12, 14 articulate at a pair of facet joints 24.

FIGS. 1-9 illustrate an exemplary spinous process implant 100. The implant 100 includes a spacer 102 positioned between the spinous processes 20, 21. The height 104 of spacer 102 limits how closely the spinous processes 20, 21 can move together. Thus, the spacer 102 maintains a minimum distance between the spinous processes 20, 21. In the case of spine disease involving posterior subsidence of the adjacent vertebra, insertion of the spacer 102 between the spinous processes 20, 21 will move the vertebrae apart and relieve pressure on nerve tissue and the facet joints 24.

Figure 3:
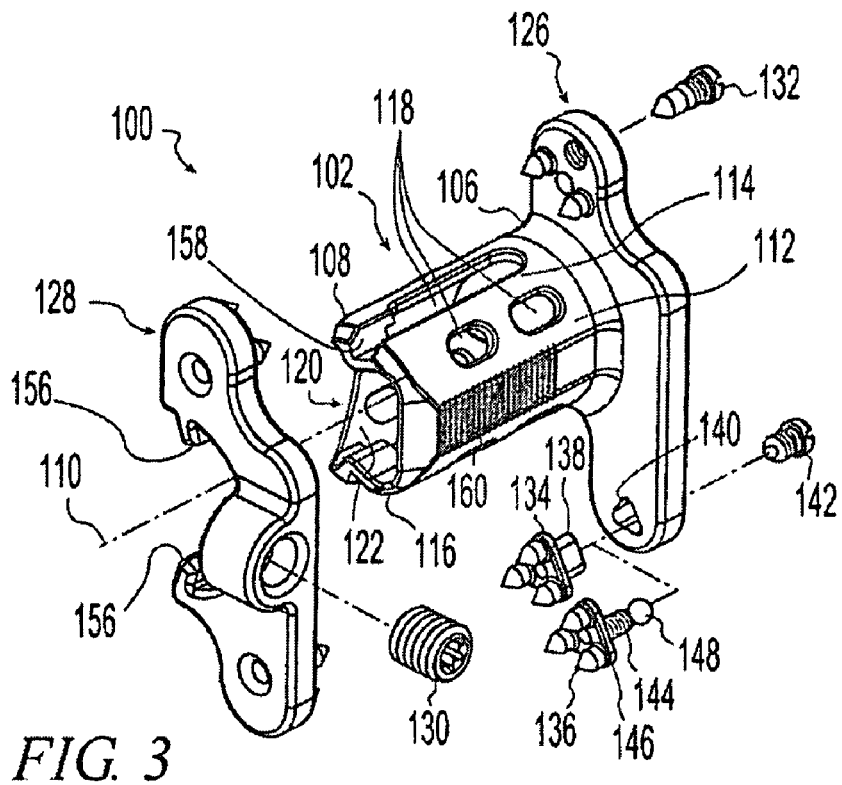
FIG. 3 is a an exploded perspective view of the implant of FIG. 1.

As shown in FIG. 3, the spacer 102 includes a first end 106, a second end 108, and a longitudinal axis 110 extending from the first end to the second end. The spacer 102 has a sidewall 112, generally parallel to the longitudinal axis 110, including superior and inferior outer surfaces 114, 116. Transverse openings 118 (see also FIG. 6) communicate from the superior and inferior outer surfaces 114, 116 inwardly to facilitate tissue in-growth. The exemplary spacer 102 includes a hollow interior 120 bounded by an inner surface 122 such that the openings 118 communicate from the outer surface to the hollow interior 120. Bone growth promoting substances 124 are shown packed into the hollow interior 120 in FIGS. 1 and 2 to promote fusion of the vertebrae 12, 14 by bone growth between the spinous processes 20.

The spinous process implant 100 further includes a first extension 126 projecting outwardly from the spacer 102 transverse to the longitudinal axis 110 to lie generally alongside the superior spinous process. Abutment of the first extension 126 with the spinous process 20 helps to maintain the spacer 102 between the spinous processes 20. In the exemplary spinous process implant 100, the first extension 126 is fixed relative to the spacer 102 and the implant includes a second extension 128 mountable to the spacer for axial movement relative to the first extension 126. The second extension 128 may be moved toward the first extension 126 to approximate the width of the spinous process 20 and better stabilize the implant 100. It is fixed in place by tightening a set screw 130 against the spacer 102. The extensions 126, 128 include fasteners 132, 134, 136 projecting from the extensions 126, 128 to engage the spinous process 20 to fix the spacer 102 to the spinous process 20. FIG. 1 depicts additional bone growth promoting substance in the form of a strips of bone 125 sandwiched between the extensions 126, 128 along the sides of the spinous processes 20 to promote bone growth along the sides of the spinous processes to further inhance fusion of the vertebrae 12, 14. The extensions 126, 128 preferably extend inferiorly (as shown) as well as superiorly to optionally attach to the inferior spinous processes to immobilize the spinous processes 20 relative to one another while fusion takes place.

The fasteners 132, 134, and 136 may take any suitable form. They may be made integral with the extensions 126, 128 such as by machining or casting them with the extensions or they may be formed separately and permanently attached to the extensions 126, 128. Fastener 132 is a sharpened spike that threadably engages the extension 126. The threaded engagement allows the fastener 132 to be replaced with a different fastener 132. For example, the fastener 132 may be replaced by one that has a different shape, a different size, a different material, or a different surface coating. The threaded engagement also allows the fastener 132 to be adjusted to extend by varying amounts from the extension 126 to vary how it engages the bone. Thus, the fastener 132 can be adjusted to fit differently shaped bones or to penetrate into a bone by varying amounts. For example, multiple threaded fasteners 132 can be adjusted to extend by different amounts to conform to curved or angled bone. Finally, the threaded engagement allows the user to remove the fastener 132 when fixation is not desired such as when it is desired to use implant 100 in a non-fusion procedure as an extension stop without limiting flexion.

Fasteners 134 and 136 are provided as multi-spike pods allowing a plurality of spikes to be quickly adjusted, changed, or omitted. Fastener 134 includes a non-circular tab 138 engageable with a non-circular opening 140 in the extension 126. The non-circular engagement prevents the fastener 134 from rotating. The tab 138 may form a press-fit, snap-fit, or other suitable engagement with the opening 140. The tab 138 may be further secured by a supplemental screw 142. Fastener 136 includes a threaded shaft 144 threadably engaged with a base member 146 to allow the length of the fastener 136 to be adjusted. The shaft 144 engages the extension 126 in rotating and pivoting manner such that the fastener 136 can be adjusted rotationally and angularly to engage the bone surface. In the illustrative embodiment, the shaft 144 terminates in a spherical ball 148 that engages the opening 140 in a ball-and-socket arrangement for three degrees of freedom. However, any mechanism that allows any number of degrees of freedom may be used. The fastener 136 may be allowed to move in use so that as the extension 126 is pressed toward a bone the fastener 136 adjusts to the angle of the bone surface. The fastener 136 may also be secured such as by screw 142 to adjust the tension in the joint and/or to lock the fastener 136 in a predetermined orientation.

Figure 4:
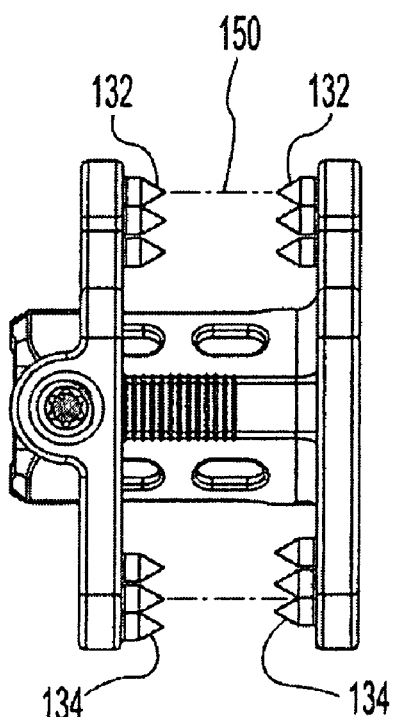
FIG. 4 is a front elevational view of the implant of FIG. 1.

FIG. 4 illustrates the axial relationship of fasteners on the opposing extensions 126, 128. In the illustrative implant 100, the fasteners 132 at the top of the implant 100 are shown aligned along a common axis 150. The fasteners 134 at the bottom of the implant 100 are shown offset so that they can interleave if necessary as they are pressed into a bone. Any combination of fastener type, number, and alignment may be provided on the implant 100.

Figure 5:
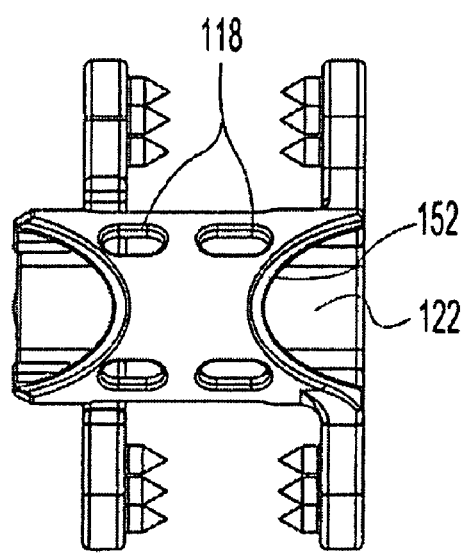
FIG. 5 is a back elevational view of the implant of FIG. 1.
Figure 6:
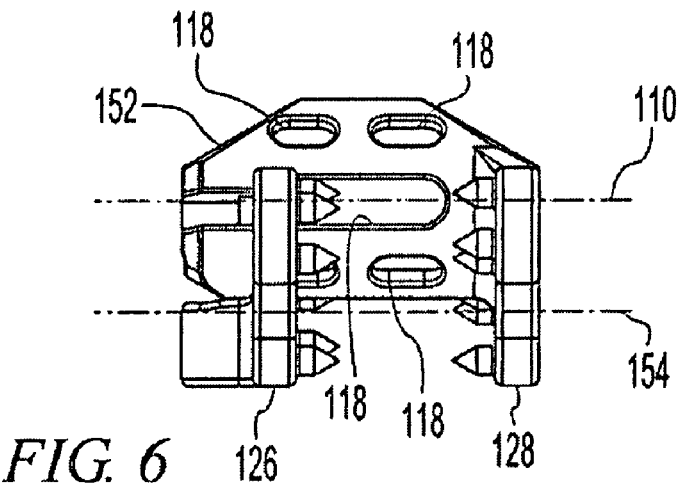
FIG. 6 is a top plan view of the implant of FIG. 1.

As seen in FIGS. 5 and 6, the ends 106, 108 of the spacer 102 include anterior chamfers 152. These chamfers 152 allow the ends 106, 108 to clear posteriorly facing structures of the vertebrae 12, 14 such as the facet joints 24. Also, as seen in FIGS. 5 and 6, the spacer 102 is offset anteriorly relative to the extensions 126, 128 such that the longitudinal axis 110 of the spacer 102 is anterior of the midline 154 of the extensions 126, 128. The anterior offset of the spacer 102 allows it to fit deeply between the spinous processes 20, 21 while the extensions 126, 128 fit alongside the spinous processes 20, 21.

Figure 7:
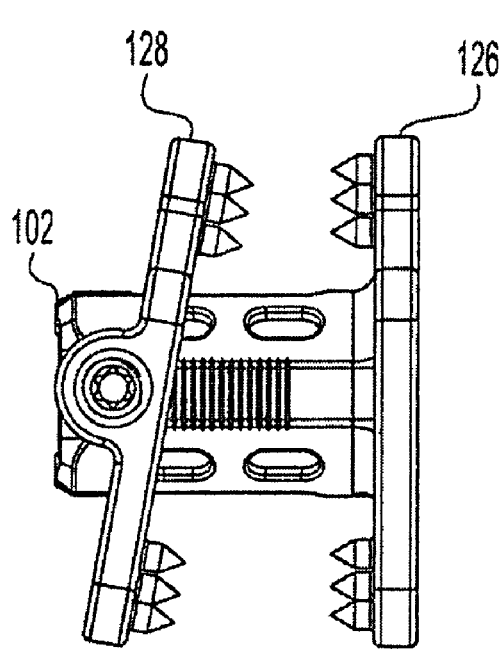
FIG. 7 is a front elevational view of the implant of FIG. 1 showing the assembly in an alternate position.
Figure 8:
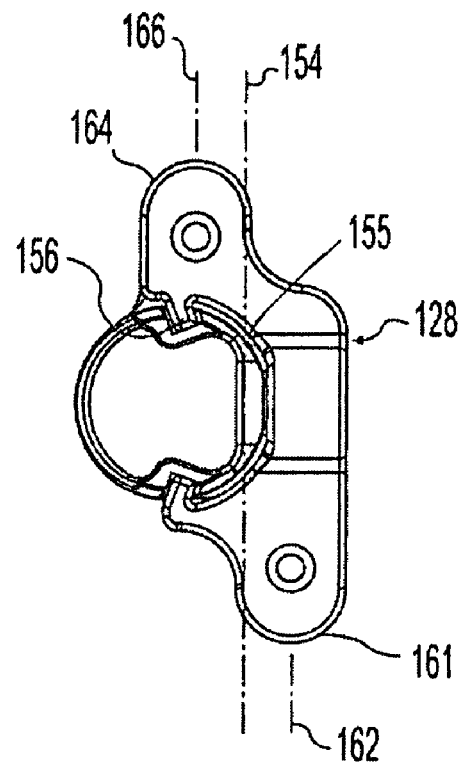
FIG. 8 is a side elevational view of the implant of FIG. 1.

As best seen in FIGS. 3 and 8, the second extension 128 defines an aperture 155 conforming generally to the cross-sectional shape of the spacer 102. In the illustrative embodiment of FIGS. 1-9, the aperture 155 opens anteriorly to form a "C"-shape. Tabs 156 extend inwardly from the superior and inferior portions of the aperture to slidingly engage elongated slots 158 in the superior and inferior surfaces of the spacer 102. The second extension 128 can be translated longitudinally toward and away from the first extension 126. Tightening the set screw 130 against the posterior side 160 of the spacer 102 forces the tabs 156 posteriorly against the sides of the slots 158 and locks the second extension 128 in place longitudinally. The posterior side 160 of the spacer 102 may be roughened as shown to better grip the set screw 130. The set screw 130 may also dig into the surface of the spacer 102 upon tightening to postitively grip the spacer 102. The aperture 155 may conform closely to the spacer 102 to constrain the second extension 128 to generally parallel motion relative to the first extension 126. Alternatively, the aperture 155 may be larger than the spacer 102 by a predetermined amount to permit a predetermined amount of angular adjustment of the second extension 128 relative to the first extension 126 as shown in FIG. 7 to allow the extension 128 to adjust to the underlying bone surface.

Figure 9:
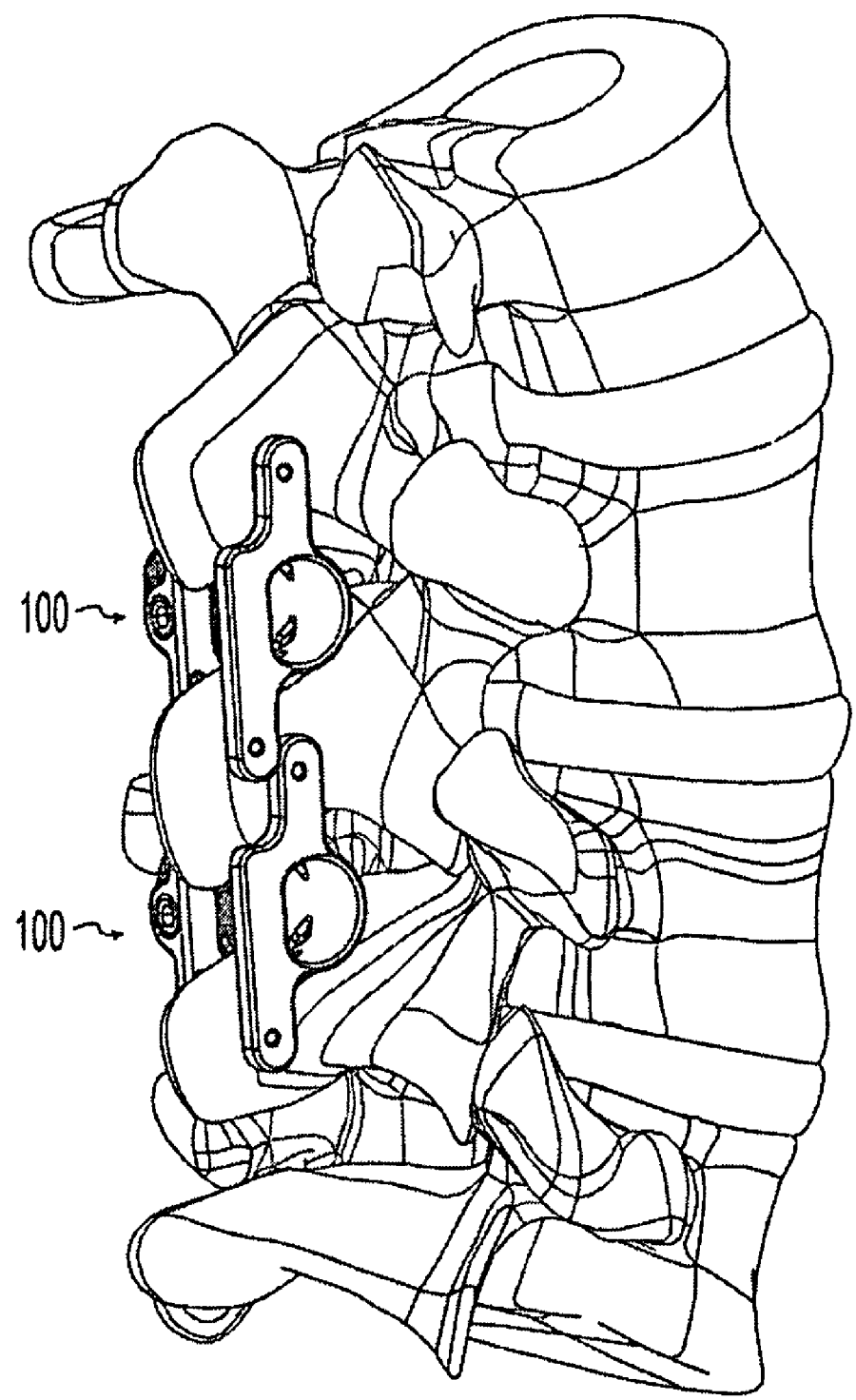
FIG. 9 is a perspective view of a pair of implants like that of FIG. 1 in situ.

As best seen in FIG. 8, the second extension 128 includes a first lobe 161 having a first lobe centerline 162 and a second lobe 164 having a second lobe centerline 166. In the illustrative embodiment, the first lobe centerline 162 and the second lobe centerline 166 are parallel and spaced apart so that the second extension 128 has a generally "Z"-shaped plan form. This shape allows the extension of one implant 100 to interleave, if necessary, with another implant 100 in a multilevel surgery as shown in FIG. 9 to permit close spacing of the implants, and/or longer extension lobes for more extensive bone engagement. In the illustrative embodiment of FIGS. 1-9, the centerlines 162 and 166 are offset equidistantly from the midline 154 of the second extension 128. The centerlines 162 and 166 may vary from parallel and they may be offset asymmetrically to form different shapes to accommodate different vertebral anatomy. For example, the shape may be tailored for different portions of the spine 10. In the illustrative embodiment of FIGS. 1-9, the first extension 126 has the same shape as the second extension 128. However, the shape may be varied between the first and second extensions 126, 128.

Figure 10:
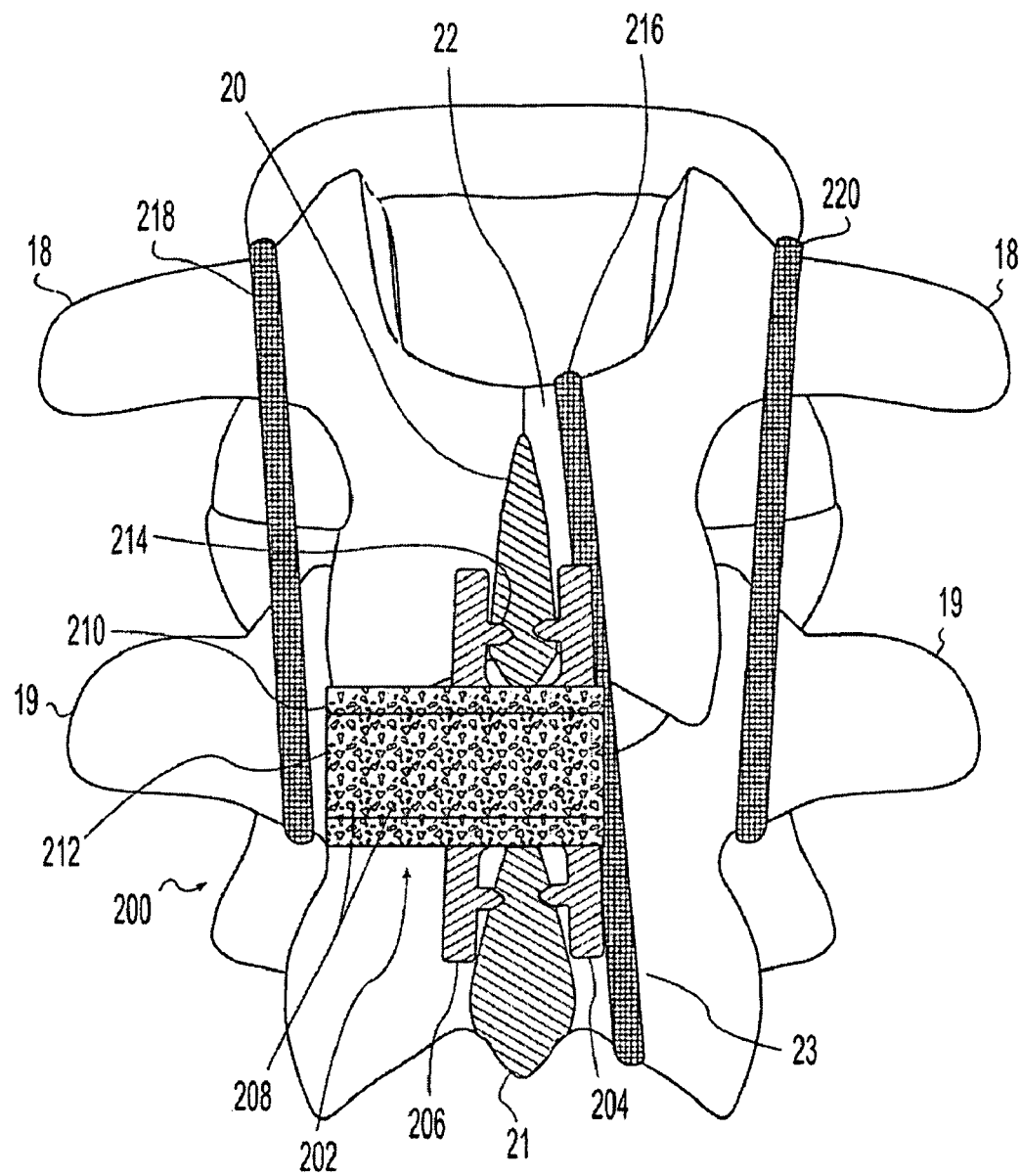
FIG. 10 is a cross sectional view of an implant like that of FIG. 1 illustrating an alternate material and cerclage elements.

FIG. 10 depicts an implant 200 having a spacer 202 and first and second extensions 204, 206. The spacer 202 includes pores 208 for tissue to grow into. The pores 208 may be individual openings spaced from one another, interconnecting openings, or combinations of individual and interconnecting openings. The spacer 202 may be a monolithic block having uniform porosity throughout. Alternatively, the spacer 202 may include an outer porous layer 210 and an inner layer 212 of different composition. For example, the inner layer 212 may be solid, porous, hollow, or some other configuration. A porous inner layer may have pores of a different size and/or distribution than the outer layer 210. Similarly, any porous portion may have uniform porosity or porosity that varies in pore size or density. A variety of pore configurations are suitable. Preferably the pore size is in the range of 1 μm to 2 mm. More preferably, the pore size is in the range of 1 μm to 500 μm. Still more preferably, the pore size is in the range of 75 μm to 300 μm. The pores may be produced by a variety of processes such as sintering of particles; leaching a soluble component from the material; matting, weaving, or otherwise combining fibers; and/or by any other known process. The pore size may be tailored to preferentially promote hard tissue growth, soft tissue growth, or a combination of hard and soft tissue growth. The extensions 204, 206 may be solid or they may have large and/or small openings to encourage bone growth in and/or around the extensions 204, 206. The spacer 202 and/or extensions 204, 206 may also be coated as previously described.

The extensions 204, 206 may be fixed and/or adjustable. In the illustrative implant 200 of FIG. 10, the first extension 204 is fixed to one end of the spacer 202 and the second extension 206 is translatable along the spacer 202 to allow the extensions to be placed adjacent the spinous processes. The extensions 204, 206 are shown with optional spikes 214 that may engage the spinous processes 20, 21 to fix the spinous processes 20, 21 relative to one another.

FIG. 10 also depicts the use of cerclage in conjunction with the implant 200. For example, one or more flexible bands 216 are placed around the lamina 22, 23 to provide a flexion stop. The band 216 may help carry the load exerted on the spikes 214 during spine flexion. Alternatively or in addition to the band 216, one or more bands 218, 220 may be placed around the transverse processes 18, 19.

Figure 11:
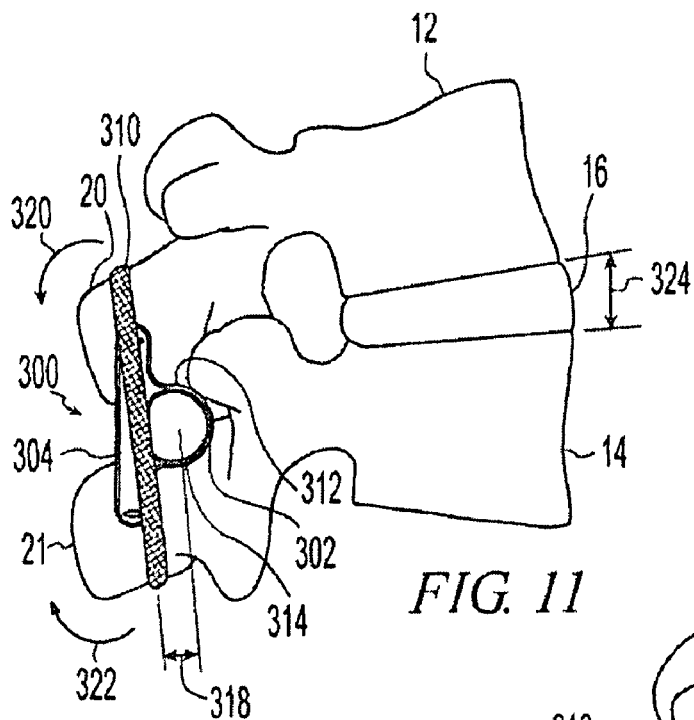
FIGS. 11-13 are side elevational views of an implant like that of FIG. 1 shown in use with cerclage elements.
Figure 12:
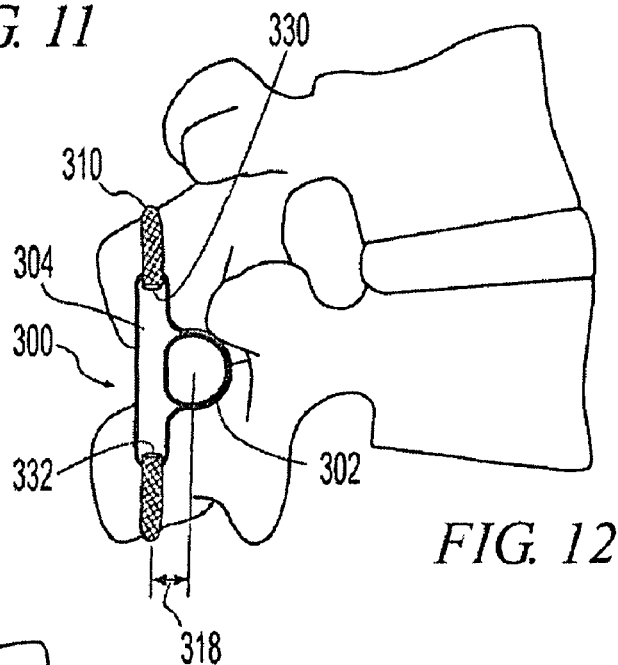
Figure 13:
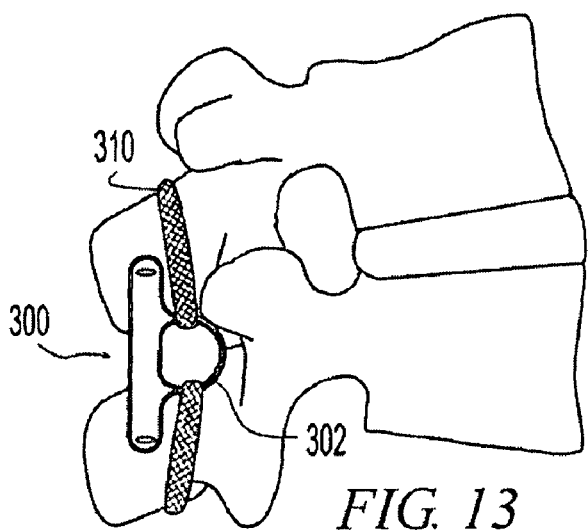

FIGS. 11-13 depict additional examples of the use of cerclage in conjunction with a spinous process implant 300 according to the present invention. The implant includes a spacer 302 for placement between adjacent spinous processes 20, 21 and an extension 304. In the example of FIG. 11, a band 310 of flexible material is looped around the spinous processes 20, 21. By placing the band 310 behind the areas 312, 314 where the spinous processes contact the spacer 302 an offset 318 is created. Tightening of the band 310 creates a moment 320, 322 on each vertebra 12, 14 that offloads some of the pressure on the disc 16 between the adjacent vertebrae 12, 14. With increased tightening of the band 310, the anterior spacing 324 of the vertebrae 12, 14 may actually be increased. Thus, by using the spinous process implant 300 in combination with the band 310, the vertebrae 12, 14 may be levered apart with the implant 300 being used as the fulcrum. In addition to the advantages already mentioned, this combination produces an anterior disc space effect with a posterior spinous process procedure that is less invasive than typical disc spacing procedures.

In the examples of FIGS. 12 and 13, the implant 300 includes a mechanism for attaching the cerclage band 310 to the implant 300. In the example of FIG. 12, the mechanism includes openings 330, 332 in the superior and inferior ends of the extension 304. By attaching the band 310 to the extension 304, the band 310 and extension 304 help stabilize one another against anterior-posterior displacement. This attachment also helps position the band 310 at a predetermined offset 318 from the spacer 302. In the example of FIG. 13, the band 310 is looped through a hollow interior of the spacer 302 itself. In this example, the band is not offset and produces minimal or no moment on the vertebrae.

Figure 14:
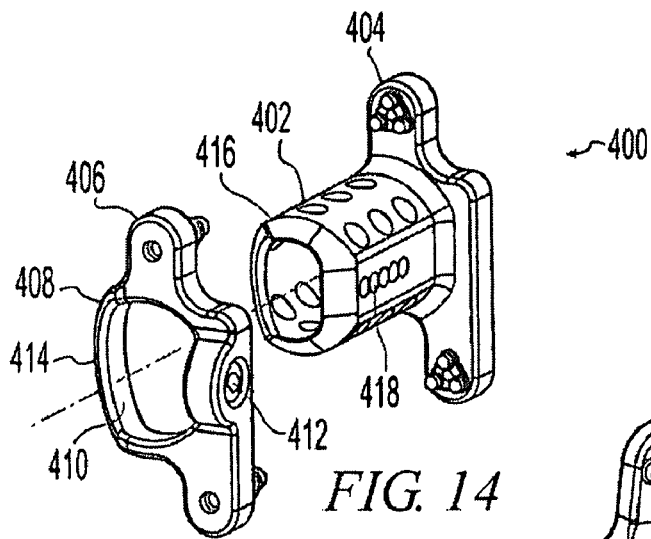
FIGS. 14-24 are perspective views of alternative embodiments of the invention.

FIGS. 14-24 illustrate alternative mechanisms for attaching a movable extension to the implant of FIG. 1. Referring to FIG. 14, an implant 400 includes a spacer 402, a first extension 404 and a second, movable extension 406. The movable extension 406 includes a body in the form of a ring 408 with an inner surface 410 generally conforming to the outer surface of the spacer 402 so that the ring is slidingly receivable on the spacer 402. A set screw 412 is tightened against the spacer 402 to fix the movable extension 406 at a desired position on the spacer 402. Tightening of the set screw 412 biases the movable extension 406 posteriorly relative to the spacer 402. The anterior portion 414 of the ring presses against the anterior portion 416 of the spacer 402 to counter this posterior bias and allow the set screw 412 to lock the extension 406. The spacer 402 may include a plurality of indentations 418 to create a positive engagement with the set screw 412 at predetermined axial locations. The ring 408 may be sized to permit a predetermined amount of tilting of the extension 406 relative to the spacer 402.

Figure 15:
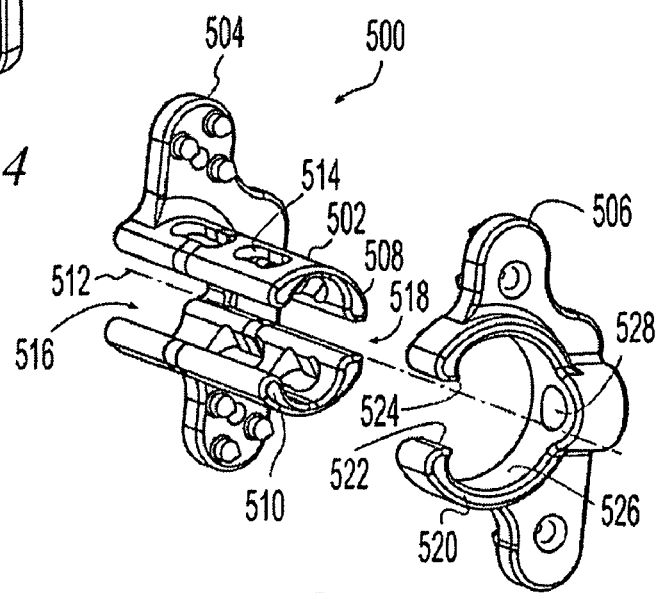

Referring to FIG. 15, an implant 500 includes a spacer 502, a first extension 504, and a second, movable extension 506. The spacer 502 includes a plurality of cantilevered beams 508, 510 projecting parallel to a longitudinal axis 512 away from the first extension 504. In the example of FIG. 15, the spacer 502 includes a pair of opposed "C"-shaped beams 508, 510 with their concave surfaces directed inwardly. The spacer 502 includes openings 514 through the beams 508, 510 and defines elongated openings 516, 518 anteriorly and posteriorly between the beams. The movable extension 506 includes a body in the form of an interrupted ring 520. The ring 520 is open anteriorly and the margins of the opening define posteriorly directed hooks 522, 524. The inner surface 526 of the ring conforms generally to the outer surface of the beams 508, 510 so that the ring is slidingly receivable on the spacer 502. The open anterior configuration of the ring 520 provides clearance to ease sliding of the ring in-vivo. A set screw 528 is tightened against the spacer 502 to fix the movable extension 506 at a desired longitudinal position on the spacer. The hooks 522, 524 curve around a portion of the anterior edge of the beams 508, 510 to resist posterior translation of the ring relative to the spacer 502 when the set screw 528 is tightened.

Figure 16:
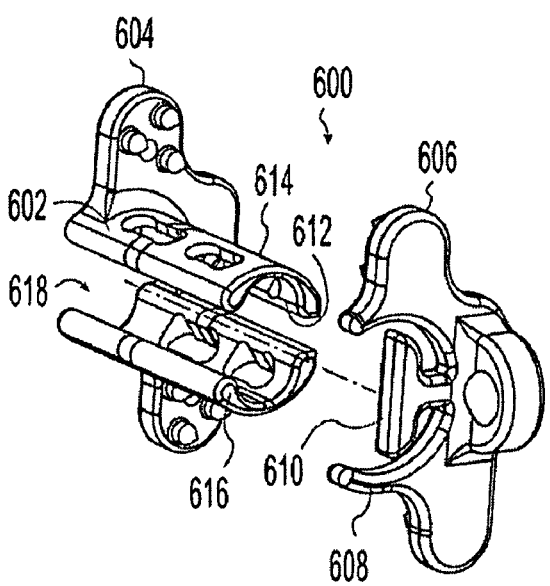

Referring to FIG. 16, an implant 600 is depicted that is similar to implant 500 of FIG. 15 having a spacer 602, first extension 604, and movable extension 606. However, the ring 608 is truncated anteriorly to provide even more anterior clearance than the ring 520 of FIG. 15. The ring 608 includes a key 610 projecting anteriorly from the posterior side of the ring 608 and expanding superiorly and inferiorly to engage the inner surface 612 of the beams 614, 616 to resist posterior translation of the ring relative to the spacer 602. The key 610 also partially blocks the hollow interior 618 of the spacer 602 to help retain material optionally packed into the interior 618.

Figure 17:
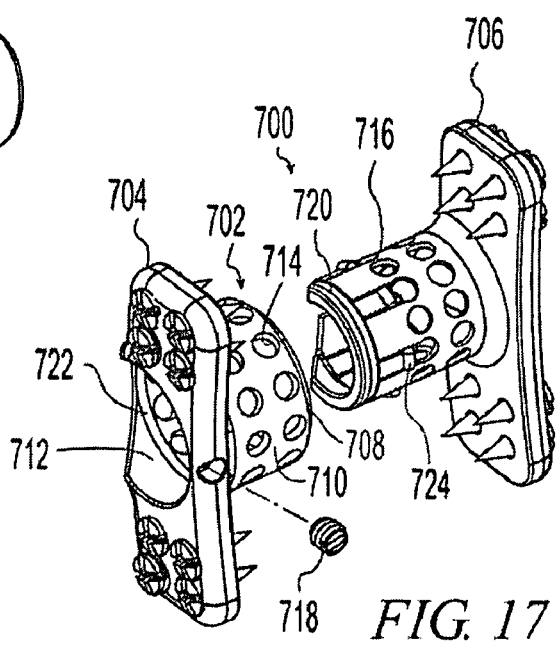

Referring to FIG. 17, an implant 700 includes a spacer 702, a first extension 704, and a second movable extension 706. The spacer 702 includes a sidewall 708 defining an outer surface 710 and an inner surface 712. In the example of FIG. 17, the spacer 702 is generally in the shape of a hollow flattened cylinder with a "D"-shaped cross section. However, the spacer 702 could be any desirable shape. The spacer 702 includes a plurality of openings 714 communicating from the outer surface 710 to the inner surface 712. The movable extension 706 includes a projection 716 configured generally like the spacer 702 but being sized to slide within the spacer 702 in telescoping relationship. The projection (or the spacer) may optionally include one or more fixation mechanisms to lock the extensions 704, 706 at a desired longitudinal spacing. Fixation mechanisms may include a set screw 718, a ridge 720 forming a snap fit with a groove 722 or other feature, a detent 724 engageable with openings 714, and/or other suitable fixation mechanisms. Any one or combinations of these mechanisms may be used and they may be reversed from the orientation shown.

Figure 18:
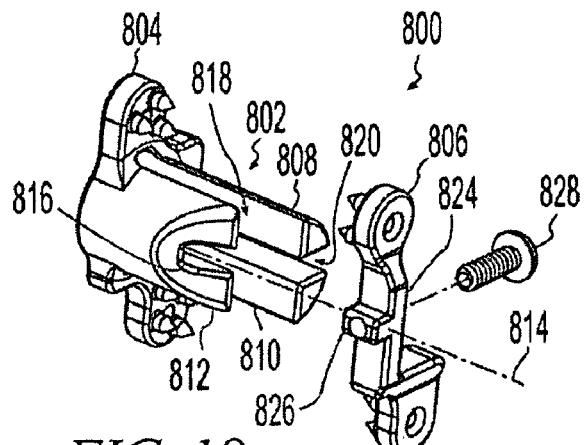
Figure 19:
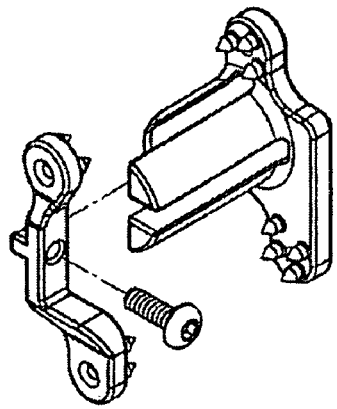
Figure 20:
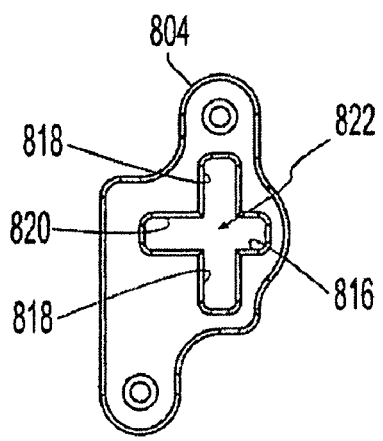

Referring to FIGS. 18-20, an implant 800 includes a spacer 802, a first extension 804, and a second, movable extension 806. The spacer 802 includes a plurality of cantilevered beams similar to FIGS. 15 and 16 except that in this example there are three beams 808, 810, 812. The beams project parallel to a longitudinal axis 814 away from the first extension 804. In the example of FIG. 18, the anterior beam 812 includes a posteriorly opening groove 816. The posterior beams 808, 810 and anterior beam 812 define an elongated slot 818 between them opening superiorly and inferiorly. The posterior beams 808, 810 further define an elongated slot 820 between them opening posteriorly. FIG. 20 illustrates a cruciform opening 822 defined by the projection of the groove 816 and slots 818, 820 projected through the first extension 804. The movable extension 806 includes a body 824 sized to slidingly engage the slot 818. An optional lug 826 can project anteriorly into groove 816 to constrain tilting of the movable extension 806 relative to the first extension 804. The lug 826 can be sized to fit closely within groove 816 to prevent tilting of the movable extension 806 or it can be sized smaller than the groove 816 to permit a predetermined amount of tilt. A set screw 828 is provided to lock the movable extension 806 to the spacer 802.

Figure 21:
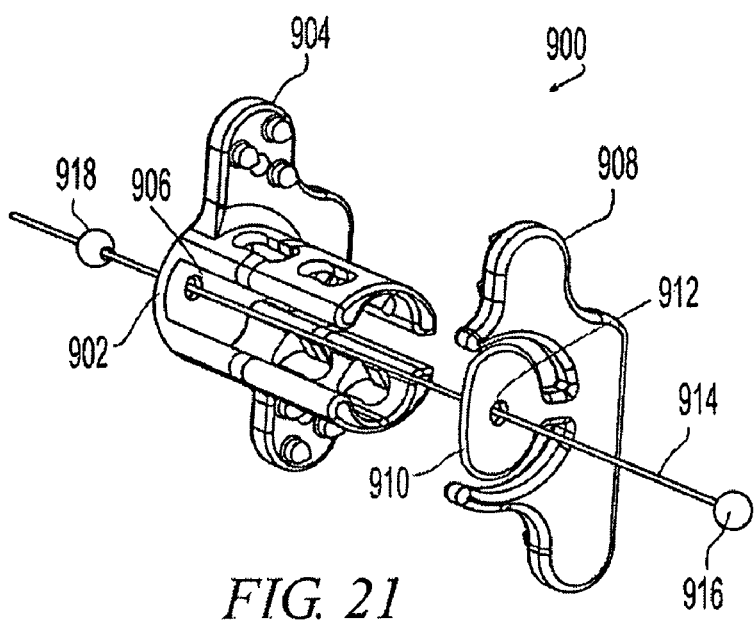

Referring to FIG. 21, an implant 900 is depicted that is configured generally like that of FIG. 16. However, an end wall 902 adjacent the first extension 904 includes a through bore 906 and the movable extension 908 includes a key 910 with a through bore 912. The bores 906, 912 receive a fastener to fix the extensions 904, 908 at a maximum spacing to prevent them from moving apart. Fasteners may include screws, bolts, nuts, cables, wires, ties, rods, and/or any other suitable fastener. In the example of FIG. 21, the fastener includes an elongated crimp receiving member 914, such as a cable, and crimp members 916, 918, such as ferrules or compressible beads.

Figure 22:
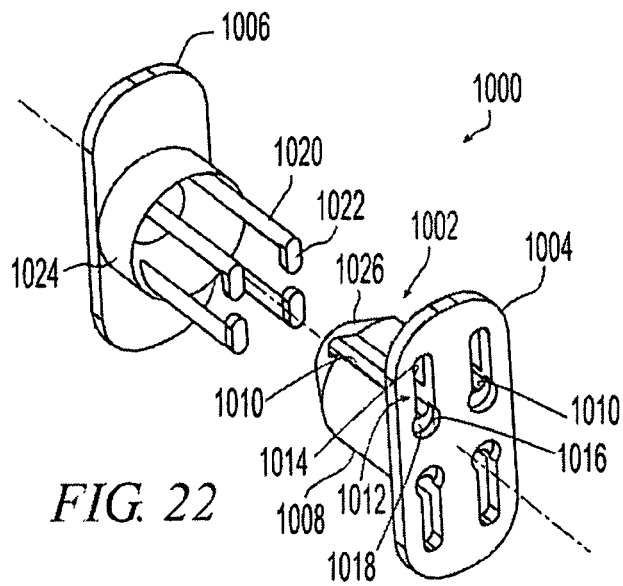

Referring to FIG. 22, an implant 1000 includes a spacer 1002, a first extension 1004, and a second extension 1006. The spacer 1002 includes an outer surface 1008 defining one or more longitudinal grooves 1010 extending along the outer surface 1008 and through the first extension 1004. The first extension 1004 includes one or more corresponding slots 1012 having a radially outwardly extending portion 1014 through the first extension 1004 and communicating with the grooves 1010. The slots 1012 have a radially inwardly extending portion 1016 defining a shoulder 1018 at the end of the grooves 1010. The second extension 1006 includes one or more corresponding projections 1020 projecting longitudinally toward the first extension 1004 and terminating at a radially inwardly directed tab 1022. The second extension 1006 further includes a centering bore 1024 having conical opening engageable with a conical free end 1026 of the spacer 1002. The second extension 1006 is attached to the spacer 1002 by pressing the tabs 1022 against the conical end 1026 of the spacer 1002 to spread the projections outwardly until the tabs 1022 engage the grooves 1010. The tabs 1022 are slid along the grooves 1010 until they exit through the slots 1012 and the tabs 1022 snap inwardly over the shoulders 1018 and into the portions 1016. Abutment of the tabs 1022 against the shoulders 1018 prevents the first and second extensions 1004, 1006 from moving apart. The engagement of the conical end 1026 of the spacer 1002 with the bore 1024 provides radial stability to the assembly.

Figure 23:
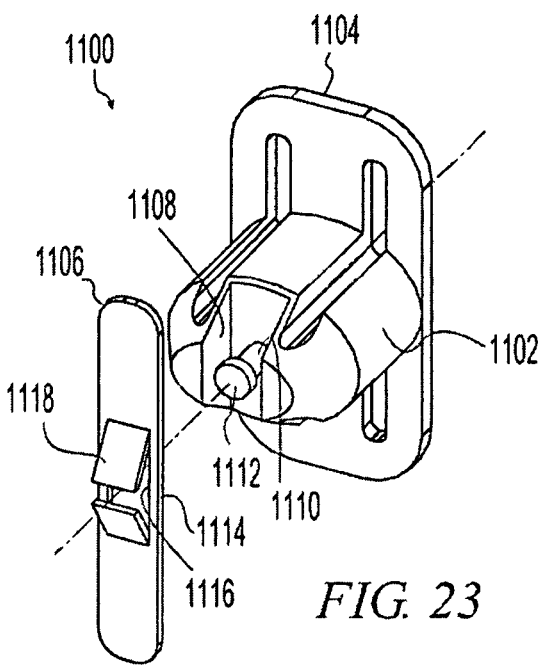

Referring to FIG. 23, an implant 1100 includes a spacer 1102, a first extension 1104, and a second extension 1106. The spacer 1102 includes a transverse groove 1108 with a central boss 1110 having an enlarged head 1112. The second extension 1106 includes a portion 1114 sized to fit within the groove 1108 and an opening 1116 bordered by one or more angled tabs 1118. The second extension 1112 is assembled to the spacer by pressing the portion 1114 into the groove 1108 with the central boss 1110 directed into the opening 1116. As the boss 1110 is pressed through the opening 1116, the tabs 1118 flex outwardly to allow it to pass. Once the boss 1110 is past the tabs 1118, the tabs 1118 return to their original position and snap behind the enlarged head 1112. In this configuration, the boss 1110 retains the second extension 1106 longitudinally and the groove 1108 prevents the second extension 1106 from rotating about the longitudinal axis of the implant 1100.

Figure 24:
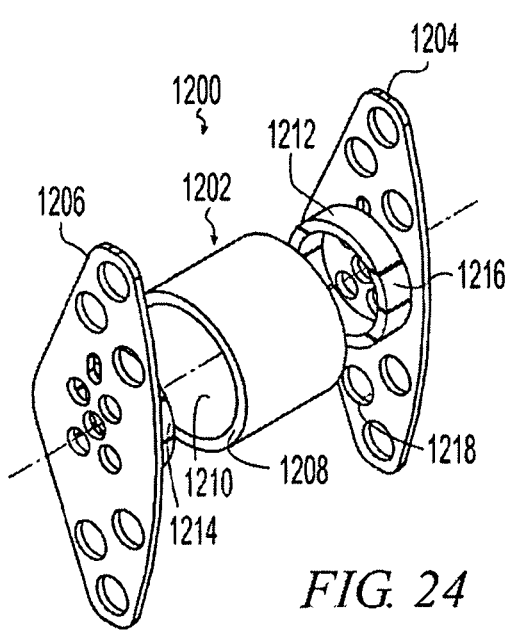

Referring to FIG. 24, an implant 1200 includes a spacer 1202, a first extension 1204, and a second extension 1206. The spacer 1202 includes a solid cylindrical sidewall 1208 defining a hollow interior 1210. The extensions 1204, 1206 are similarly configured and each includes a projection 1212, 1214 sized to fit inside of the spacer 1202. The extensions 1204, 1206 may attach to the spacer by press-fitting, snap-fitting, screwing, and/or otherwise engaging the projections 1212, 1214 with the spacer 1202. Alternatively, or additionally, the extensions 1204, 1206 may attach to the spacer 1202 with any of the previously depicted attachment mechanisms such as with a setscrew as shown in FIG. 3 or an elongated fastener as shown in FIG. 21. In the example of FIG. 24, the extensions 1204, 1206 are slotted longitudinally to form flexible petals 1216 that press into the spacer 1202. The extensions 1204, 1206 include openings 1218 to allow tissue growth, permit attachment of cerclage members, and/or receive additional fasteners attached to the spinous processes.

The spacer 1202 of FIG. 24 could have openings as shown in some of the other examples. Likewise, the other examples could have a solid surface as shown in FIG. 24. Similarly the extensions of any of the examples may be solid, have openings, or be otherwise advantageously configured.

Implants according to the present invention may be implanted using a variety of surgical approaches and techniques. Surgical approaches may include superspinous ligament sacrificing posterior approaches, superspinous ligament preserving posterior approaches, lateral approaches, and/or other suitable approaches. Techniques may include leaving the tissues at the surgical site unmodified or modifying the tissues such as trimming, rasping, roughening, and/or otherwise modifying them. For example, in FIG. 1, a lateral approach is used and the inferior spinous process is cut on its superior surface 26 to enlarge the interspinous space to receive the implant 100. After the interpinous space is prepared, the spacer 102 is inserted into the interspinous space. If a first extension 126 is present it may be pressed inwardly to lie near or abut one or more spinous processes. If a second extension 128 is used, it is engaged with the spacer 102 and also optionally pressed inwardly. In FIG. 1, opposing extensions 126, 128 having inwardly directed bone fasteners have been used and pressed inwardly so that the fasteners 132 engage the spinous processes 20, 21. The engagement of the fasteners 132 with the inferior spinous process 21 is not shown in FIG. 1 because the extensions are offset superiorly and inferiorly as shown in FIGS. 3, 8, and 9.

Figure 25:
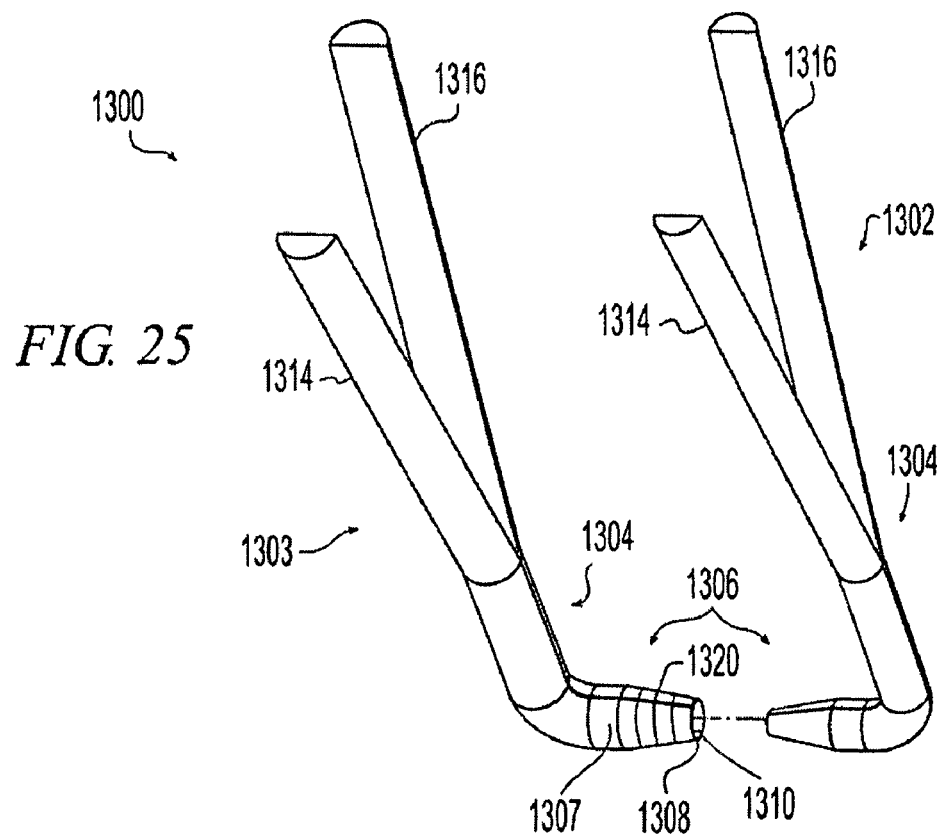
FIG. 25 is a perspective view of instrumentation for implanting the implant of FIG. 1.
Figure 26:
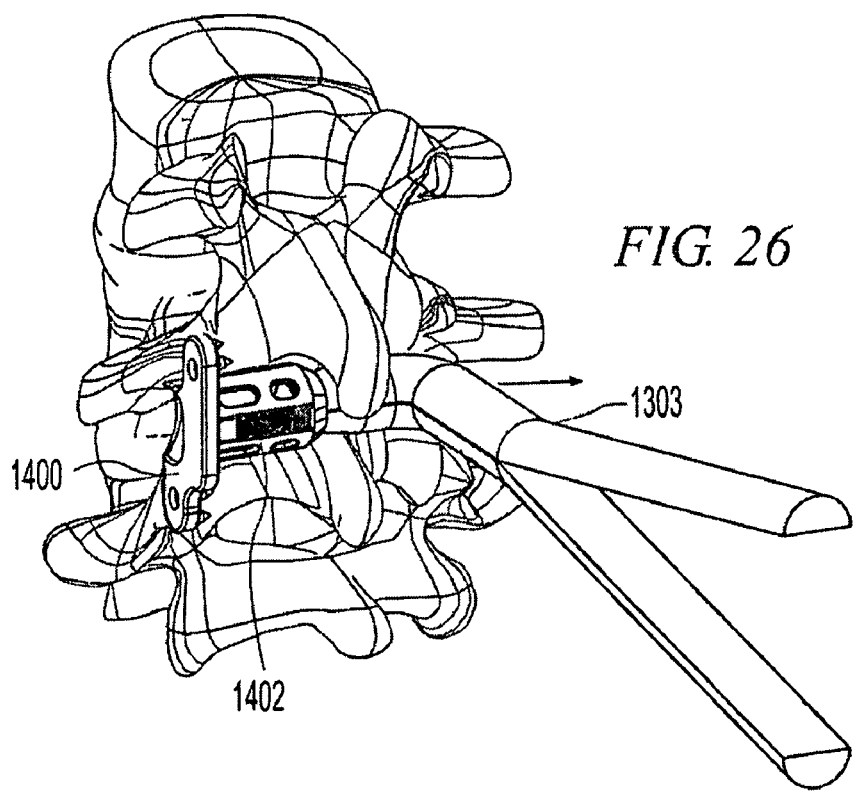
FIG. 26 is a perspective view of the instrumentation of FIG. 25 in use to implant the implant of FIG. 1.

Referring to FIGS. 25 and 26, a set of instruments 1300 is provided to facilitate lateral insertion of an implant into the interspinous space. The set of instruments includes a plurality of inserters 1302, 1303 in which each inserter 1302, 1303 has a first or handle portion 1304 and a second or working portion 1306. The working portion 1306 is insertable into the interspinous space. Preferably, the handle portion 1304 extends transverse to the working portion 1306 to facilitate holding and manipulating the inserter 1302, 1303 while the working portion 1306 is in the interspinous space. The handle portion 1304 and working portion 1306 may define a curve, angle, offset, and/or any other suitable transverse orientation. In the example of FIG. 25, the inserters 1302, 1303 are generally "L"-shaped. The working portion 1306 tapers from a relatively larger cross-sectional dimension at a first portion 1307 spaced away from its free end 1308 to a relatively smaller cross-sectional dimension at its free end 1308. In the illustrative embodiment, the working portion is conical and tapers from a larger diameter to a smaller diameter. The end 1308 defines a hollow tip having an opening 1310. The set of instruments 1300 is provided with a plurality of similarly configured inserters having differently sized working portions 1306 such that the end 1308 of one inserter 1302 will fit inside the opening 1310 at the tip of another inserter 1303. Optionally, the working portion 1306 may be separated into opposing halves attached to opposing handles 1314, 1316. As the opposing handles 1314, 1316 are moved relative to one another, the opposing halves of the working portion 1306 move relative to one another. In the illustrative embodiment, squeezing the handles 1314, 1316 toward one another causes the working portion 1306 to expand as the opposing halves of the working portion 1306 open outwardly away from one another.

In use, a first inserter 1302 is inserted into the interspinous space. The first inserter 1302 is relatively small to ease insertion. As the end 1308 is inserted further, the tapered working portion 1306 expands the interspinous space. Optionally, the interspinous space can be further expanded by expanding the working portion while it is inside the interspinous space such as by squeezing the handles 1314, 1316. A second, larger inserter 1302 is engaged with the first inserter 1303 by placing its hollow tip over the tip of the first inserter 1303 and then passing the overlapping instruments back through the interspinous space to remove the first inserter 1303 and insert the second inserter 1302. As the end of the second inserter 1303 is inserted further, the tapered working portion expands the interspinous space. Optionally, the interspinous space can be further expanded by expanding the working portion while it is inside the interspinous space. Progressively larger inserters can be inserted in this fashion until the interspinous space has been expanded to the desired size. Once the desired size has been reached the appropriate implant size may be determined by noting the size of the last inserter. The inserter may optionally include indicia 1320 on the tapered working end corresponding to different spacer sizes to further facilitate sizing the implant. The implant is inserted by engaging the spacer 1402 with the working end of the inserter as shown in FIG. 26. The implant may be engaged inside of the hollow tip of the inserter or the tip of the inserter may engage a hollow tip on the implant as shown. The spacer 1402 is pressed into the interspinous space as the inserter is withdrawn.

Although examples of a spinous process implant and associated instruments and techniques have been described and illustrated in detail, it is to be understood that the same is intended by way of illustration and example only and is not to be taken by way of limitation. Accordingly, variations in and modifications to the spinous process implant, instruments, and technique will be apparent to those of ordinary skill in the art, and the following claims are intended to cover all such modifications and equivalents.

What is claimed is:

1. An implant for placement between spinous processes of adjacent vertebrae of a spine, the implant comprising:
 a spacer with a first end, a second end, and a longitudinal axis extending from the first end to the second end, the spacer having a sidewall generally parallel to the longitudinal axis and having superior and inferior surfaces operable to abut the spinous processes and maintain the spinous processes in a spaced apart relationship, the superior and inferior surfaces being spaced apart a distance corresponding to a predetermined minimum spacing between the spinous processes, the spacer comprising a plurality of channels;
 a first extension integral with and, projecting from the first end of the spacer transverse to the longitudinal axis to lie generally alongside the spinous processes of adjacent vertebrae; and
 a second extension opposing the first extension, the second extension defines an aperture that opens in an anterior direction and comprises a plurality of opposing tab members adapted to directly engage the plurality of channels of the spacer and be translated over an outer surface of the spacer from the spacer second end toward the first extension;
 wherein at least one of the first and second extensions further comprise at least one fastener adapted to engage the spinous processes to fix the spacer to the spinous processes and limit a maximum spacing between the spinous processes, such that the predetermined minimum spacing between the spinous processes is substantially equal to the maximum spacing between the spinous processes.

2. The implant of claim 1 wherein the first extension includes the at least one fastener adapted to engage at least one of the spinous processes to fix the spacer to the spinous processes.

3. The implant of claim 2 wherein the at least one fastener is a spike.

4. The implant of claim 2 wherein the at least one fastener is a tooth.

5. The implant of claim 2 wherein the at least one fastener is a screw.

6. The implant of claim 2 wherein the at least one fastener is selected from the group consisting, of: hooks, bolts, adhesives, or clamps.

7. The implant of claim 2 wherein the at least one fastener is adapted to bite into at least one of the spinous processes.

8. The implant of claim 1 wherein the spacer and first extension comprise a first relatively softer material and the fastener comprises a second relatively harder material.

9. The implant of claim 1 wherein the second extension includes the at least one fastener adapted to engage at least one of the spinous processes to fix the spacer to the spinous processes.

10. The implant of claim 1 wherein the at least one fastener comprises a plurality of fasteners on both of the first and second extensions, wherein the, fastener on the first extension is adapted to be offset relative to the fastener on the second extension when the fasteners are engaged with the spinous processes.

11. The implant of claim 1 wherein the at least one fastener is adjustable angularly relative to the extension to which it is attached such that the at least one fastener is non-normal to the extension.

12. The implant of claim 1 wherein the at least one fastener is adjustable to vary the distance it extends from the extension to which the at least one fastener is attached.

13. The implant of claim 1 wherein the at least one fastener is removable from the extension to which it is attached.

14. The implant of claim 1 wherein the at least one fastener comprises a plurality of fasteners connected together at a common base, the common base being removably engageable with the extension to which it is attached.

15. The implant of claim 1 wherein the first extension has a first portion extending superiorly and a second portion extending inferiorly, the superior and inferior portions being offset anteriorly-posteriorly relative to one another to define a generally "Z"-shaped offset, the extensions of multiple implants placed in adjacent interspinous spaces being able to interleave.

16. The implant of claim 1 wherein the spacer includes an anterior side between the superior and inferior surfaces facing anteriorly when the superior and inferior surfaces are abutting the spinous processes, the spacer having anteriorly facing chamfers at its first and second ends.

17. The implant of claim 1 wherein the superior and inferior surfaces of the spacer have a midline and the first extension is offset posteriorly of the midline so that the spacer is positioned relatively more anteriorly and the extension is positioned, relatively more posteriorly.

18. The implant of claim 1, wherein the second extension includes a projection and the first extension defines an opening engageable with the projection in a snap fitting relationship.

19. The implant of claim 1 wherein the second extension includes a plurality of fasteners to fix the spacer to the spinous processes.

20. The implant of claim 1 wherein the second extension is angularly adjustable with respect to the first extension.

21. The implant of claim 1 comprising a set screw such that the set screw locks the second extension to the spacer.

22. A method of treating spine disease comprising:
 providing a spacer having a first end, a second end, and a longitudinal axis extending from the first end to the second end, the spacer having a sidewall generally parallel to the longitudinal axis and having superior and inferior outer surfaces adapted to abut the spinous processes and maintain the spinous processes in a spaced apart relationship, the sidewall comprising at least two elongated slots, the superior and inferior outer surfaces being spaced apart a distance corresponding to a desired minimum spacing between the spinous processes, a first extension extending superiorly and inferiorly outwardly from the spacer transverse to the longitudinal axis to lie generally alongside the spinous processes, a second extension extending superiorly and inferiorly outwardly from the spacer transverse to the longitudinal axis to lie generally alongside the spinous processes opposite the first extension, the second extension defining an aperture having at least two tab members connectable with the at least two elongated slots and being axially translatable toward and away from the first extension;
 inserting the spacer between spinous processes of adjacent vertebrae to provide both an extension stop and a flexion stop;

positioning the second extension at least partially over the superior and inferior outer surfaces of the spacer and inter-engaging the second extension directly to the spacer;

translating the second extension axially towards the first extension so as to slide the second extension over a portion of the spacer to cause the first and second extension to engage with the spinous processes to fix the spacer to the spinous processes; and locking the, second extension at a desired location along the spacer relative to the first extension.

23. The method of claim 22 further comprising:

fastening the extensions rigidly to the spinous processes; and permitting the adjacent vertebrae to fuse to one another.

24. The method of claim 22 further comprising adjusting the angular placement of the second extension with respect to the first extension.

25. An implant for placement between spinous processes of adjacent vertebrae of a spine, the implant comprising:

a spacer with a first end, a second end, and a longitudinal axis extending from the first end to the second end, the spacer having superior and inferior surfaces generally parallel to the longitudinal axis and operable to abut the spinous processes and maintain the spinous processes in a spaced apart relationship, the superior and inferior surfaces being spaced apart a distance corresponding to a predetermined minimum spacing between the spinous processes, the spacer comprising at least two elongated slots arranged in an opposing manner and extending from a terminal portion of the second end towards the first end;

a first extension coupled to the first end of the spacer and projecting from the spacer transverse to the longitudinal axis to lie generally alongside the spinous processes of adjacent vertebrae, the first extension comprising at least one fastener projecting towards the second end and being adapted to fixedly engage with the spinous processes and limit the maximum spacing between the spinous processes;

a second extension defining an aperture that opens in an anterior direction and comprising at least two tabs, the at least two tabs being receivable in the at least two elongated slots at the second end, the second extension opposing the first extension, the second extension being axially translatable toward and away from the first extension by sliding the at least two tabs in the at least two elongated slots, the second extension comprising at least one fastener projecting towards the first end and being adapted to fixedly engage with the spinous processes; and a set screw extendible through an opening in the second extension to engage the sidewall of the spacer and lock the second extension in a position such that the fasteners bite into the spinous processes.

26. The implant of claim 25 wherein the spacer comprises a generally hollow spacer having a sidewall defining the superior and inferior surfaces.

27. A spinal implant, comprising:

a substantially hollow spacer having upper and lower wall portions adapted to abut spinous processes of adjacent vertebrae, the spacer further comprising a first end, a second end, a longitudinal axis extending from the first and second ends, and a plurality of longitudinally extending slots;

a first extension member extending from the first end of the spacer generally transverse to the longitudinal axis, the first extension member adapted to lie alongside the spinous processes of adjacent vertebrae when the upper and lower spacer wall portions abut the spinous processes;

a second extension member defining an aperture that opens anteriorly to form a generally C-shaped cross section when viewed along the longitudinal axis. the second extension further comprises a plurality of tabs adjacent the aperture that extend inwardly toward the longitudinal axis and engage the plurality of longitudinally extending slots, the second extension is adapted to directly engage the spacer at the second end and be translated over an outside surface of the spacer towards the first extension, the second extension member adapted to lie alongside the spinous processes of adjacent vertebrae when the upper and lower spacer wall portions abut the spinous processes; and means for, fixedly coupling at least one of the first and second extension members to the spinous processes to maintain the spinous processes in a fixed, spaced apart relationship abutting the spacer.

28. The spinal implant of claim 27, wherein the means for fixedly coupling comprises at least one spike extending from the first extension member, the at least one spike adapted to bite into at least one of the adjacent spinous processes.

29. The spinal implant of claim 27, wherein the means for fixedly coupling comprises at least one spike extending from the second extension member, the at least one spike adapted to bite into at least one of the adjacent spinous processes.

30. The spinal implant of claim 27, wherein the means for fixedly coupling comprises a plurality of spikes extending from the first and second extension members, the plurality of spikes adapted to bite into the adjacent spinous processes.

31. The spinal implant of claim 27, wherein the spacer upper and lower wall portions each comprise at least one opening adapted to permit bony growth therethrough.

32. The spinal implant of claim 27, further comprising a bone growth promoting substance at least partially filling the hollow spacer.

33. The spinal implant of claim 27 further comprising means for fixedly coupling the second extension to the spacer at a desired distance from the first extension.

34. The spinal implant of claim 33 wherein the first and second extensions are generally parallel when the second extension is fixedly coupled to the spacer.

35. The spinal implant of claim 27, wherein the two tab members are oriented at an angle to each other.

* * * * *